(12) United States Patent
Eddaoudi et al.

(10) Patent No.: US 10,328,380 B2
(45) Date of Patent: Jun. 25, 2019

(54) METAL ORGANIC FRAMEWORK ABSORBENT PLATFORMS FOR REMOVAL OF CO2 AND H2S FROM NATURAL GAS

(71) Applicants: King Abdullah University of Science and Technology, Thuwal (SA); SAUDI ARABIAN OIL COMPANY, Dhahran (SA)

(72) Inventors: Mohamed Eddaoudi, Thuwal (SA); Amandine Cadiau, Thuwal (SA); Prashant M. Bhatt, Thuwal (SA); Karim Adil, Thuwal (SA); Youssef Belmabkhout, Thuwal (SA)

(73) Assignees: SAUDI ARABIAN OIL COMPANY, Dhahran (SA); KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/564,935

(22) PCT Filed: Apr. 7, 2016

(86) PCT No.: PCT/IB2016/051987
§ 371 (c)(1),
(2) Date: Oct. 6, 2017

(87) PCT Pub. No.: WO2016/162830
PCT Pub. Date: Oct. 13, 2016

(65) Prior Publication Data
US 2018/0093218 A1    Apr. 5, 2018

Related U.S. Application Data

(60) Provisional application No. 62/144,175, filed on Apr. 7, 2015.

(51) Int. Cl.
*B01D 53/02* (2006.01)
*B01D 53/52* (2006.01)
(Continued)

(52) U.S. Cl.
CPC ............ *B01D 53/02* (2013.01); *B01J 20/226* (2013.01); *B01J 20/28057* (2013.01);
(Continued)

(58) Field of Classification Search
None
See application file for complete search history.

(56) References Cited

U.S. PATENT DOCUMENTS 5,376,614 A    12/1994 Birbara et al.
5,876,488 A    3/1999 Birbara et al.
(Continued)

FOREIGN PATENT DOCUMENTS

WO    2014074679 A1    5/2014

OTHER PUBLICATIONS

Cadiau, et al., "ZnAlF5'[TAZ]: an Al fluorinated MOF of MIL-53(Al) topology with cationic {Zn(1,2,4 triazole)}2+ inkers", Journals of Materials Chemistry, vol. 21, 2011, 3949-3951.
(Continued)

*Primary Examiner* — Daniel Berns
(74) *Attorney, Agent, or Firm* — Billion & Armitage; Benjamin C. Armitage

(57) ABSTRACT

Provided herein are metal organic frameworks comprising metal nodes and N-donor organic ligands which have high selectivity and stability in the present of gases and vapors including $H_2S$, $H_2O$, and $CO_2$. Methods include capturing one or more of $H_2S$, $H_2O$, and $CO_2$ from fluid compositions, such as natural gas.

17 Claims, 12 Drawing Sheets

(51) Int. Cl.
  B01D 53/62    (2006.01)
  B01D 53/72    (2006.01)
  B01D 53/80    (2006.01)
  B01D 53/81    (2006.01)
  B01D 53/96    (2006.01)
  B01J 31/16    (2006.01)
  B01J 20/22    (2006.01)
  B01J 20/28    (2006.01)
  B01J 20/34    (2006.01)
  C07F 5/06     (2006.01)
  C07F 9/00     (2006.01)
  C07F 15/02    (2006.01)
  C07F 15/04    (2006.01)

(52) U.S. Cl.
  CPC ..... B01J 20/28069 (2013.01); B01J 20/3425 (2013.01); B01J 20/3483 (2013.01); B01J 20/3491 (2013.01); C07F 5/066 (2013.01); C07F 9/00 (2013.01); C07F 15/02 (2013.01); C07F 15/04 (2013.01); B01D 2253/116 (2013.01); B01D 2253/204 (2013.01); B01D 2256/245 (2013.01); B01D 2257/304 (2013.01); B01D 2257/504 (2013.01); B01D 2257/80 (2013.01); B01D 2259/40007 (2013.01); Y02C 10/08 (2013.01)

(56) References Cited

U.S. PATENT DOCUMENTS 9,138,719 B1     9/2015  Eddaoudi et al.
2017/0137450 A1  5/2017  Eddaoudi et al.
2017/0247622 A1  8/2017  Eddaoudi et al.

OTHER PUBLICATIONS

Gautier, et al., "On the Origin of the Differences in Structure Directing Properties of Polar Metal Oxyfluoride [MOxF6-x]2-(x=1,2) Building Units", Inorganic Chemistry, Jan. 22, 2015, 1712-1719.
Notification of Transmittal of the International Search Report and the Written Opinion of the International Searching Authority, or the Declaration for PCT/IB2016/051987, dated Sep. 7, 2016.
Babarao, et al., "Molecular screening of metal-organic frameworks for CO2 storage", Langmuir, 24, 2008, 6270-6278.
Bae, et al., "Carborane-based metal-organic frameworks as highly selective sorbents for CO2 over methane", Chem. Commun., 2008, 4135-4137.
Banerjee, et al., "Control of Pore Size and Functionality in Isoreticular Zeolitic Imidazolate Frameworks and their Carbon Dioxide Selective Capture Properties", JACS Communications, 2009, 3875-3877.
Banerjee, et al., "High-Throughput Synthesis of Zeolitic Imidazolate Frameworks and Application to CO2 Capture", Science, Feb. 15, 2008, 939-943.
Barcia, et al., "Single and multicomponent sorption of CO2, CH4 and N2 in a microporous metal-organic framework", Sep. Sci. Technol. 43,, 2008, 3494-3521.
Bastin, et al., "A Microporous Metal-Organic Framework for Separation of CO2/N2 and CO2/CH4 by Fixed-Bed Adsorption", J. Phys. Chem., 2008, 1575-1581.
Belmabkhout, et al., "Amine-Bearing Mesoporous Silica for CO2 and H2S Removal from Natural Gas and Biogas", Langmuir Letter, 2009, 13275-13278.
Belmabkhout, et al., "Isothermal versus Non-isothermal Adsorption-Desorption Cycling of Triamine-Grafted Pore-Expanded MCM-41 Mesoporous Silica for CO2 Capture from Flue Gas", Energy&Fuels article, American Chemical Society, 2010, 5273-5280.
Belmabkhout, et al., "Simultaneous Adsorption of H2S and CO2 on Triamine-Grafted Pore-Expanded Mesoporous MCM-41 Silica", energy&fuels, ACS Publications, 2011, 1310-1315.
Britt, et al., "Highly efficient separation of carbon dioxide by a metal-organic framework replete with open metal sites", Dec. 8, 2009, 20637-20640.
Burd, et al., "Highly Selective Carbon Dioxide Uptake by [Cu(bpy-n)2(SiF6)] (bpy-1=4,4'-Bipyridine; bpy-2=1,2-Bis(4-pyridyl)ethene)", Journal of the American Chemical Society, Feb. 8, 2012, 3663-3666.
Cadiau, et al., "Hydrothermal synthesis, ab-initio structure determination and NMR study of the first mixed Cu—Al fluorinated MOF", CrystEngComm, The Royal Society of Chemistry, 2013, 3430-3435.
Caskey, et al., "Dramatic Tuning of Carbon Dioxide Uptake via Metal Substitution in a Coordination Polymer with Cylindrical Pores", JACS Communications, 2008, 10870-10871.
Chue, et al., "Comparison of Activated Carbon and Zeolite 13X for COa Recovery from Flue Gas by Pressure Swing Adsorption", Ind. Eng. Chem. Res., 1995, 591-598.
Finsy, et al., "Separation of CO2/CH4 mixtures with the MIL-53(Al) metal-organic", Microporous and Mesoporous Materials, 2009, 221-227.
Furukawa, et al., "Storage of Hydrogen, Methane, and Carbon Dioxide in Highly Porous Covalent Organic Frameworks for Clean Energy Applications", JACS Article, American Chemical Society, 2009, 8875-8883.
Gautier, et al., "Orientatinal order of [VOF5]2- and [NbOF5]2-polar units in chains", Journal of Solid State chemistry, vol. 195,, Jan. 24, 2012, 132-139.
Halasyamani, et al., "Syntheses and Structures of Two New Cu/Nb/pyrazine Complexes: Three Dimensional CuNb(pyz)20F5-(pyz)(H2O) and Two Dimensional [Cu(pyz)2.5]+[NbF6-(Pyz)]", Zeitschrift fur anorganische und allgemeine Chemie, 1996, 479-485.
Hamon, et al., "Comparative Study of Hydrogen Sulfide Adsorption in the MIL-53(Al, Cr, Fe), MIL-47(V), MIL-100(Cr), and MIL-101(Cr) Metal-Organic Frameworks at Room Temperature", JACS Communications, Mar. 2, 2009, 8775-8777.
Hao, et al., "Upgrading low-quality natural gas with H2S- and CO2-selective polymer membranes Part I. Process design and economics of membrane stages without recycle streams", Journal of Membrane Science, 2002, 177-206.
Heier, et al., "The Polar [WO2F4]2-Anion in the Solid State", Inorg. Chem., 1999, 762-767.
Hook, et al., "An Investigation of Some Sterically Hindered Amines as Potential Carbon Dioxide Scrubbing Compounds", Ind. Eng. Chem. Res., 1997, 1779-1790.
Li, et al., "Gas Adsorption and Storage in Metal-Organic Framework MOF-177", Langmuir, 2007, 12937-12944.
Lin, et al., "Microporosity, Optical Bandgap Sizes, and Photocatalytic Activity of M(I)-Nb(V) (M=Cu, Ag) Oxyfluoride Hybrids", Crystal Growth & Design, vol. 10, No. 3, 2010, 1323-1331.
Llewellyn, et al., "High Uptakes of CO2 and CH4 in Mesoporous Metal-Organic Frameworks MIL-100 and MIL-101", Langmuir, American Chemical Society, 2008, 7245-7250.
Maggard, et al., "Understanding the Role of Helical Chains in the Formation of Noncentrosymmetric Solids", American Chemical Society, 2001, 7742-7743.
Mandal, et al., "Simultaneous absorption of CO2 and H2S into aqueous blends of N-methyldiethanolamine and diethanolamine", Environ. Sci. Technol. 2006, 40, 6076-6084.
Noro, et al., "A New, Methane Adsorbent, Porous Coordination Polymer [{CuSiF6(4,4'-bipyridine)2}n]", Angew. Chem. int. Ed., 2000, 2081-2084.
Noro, et al., "Framework Engineering by Anions and Porous Functionalities of Cu(II)/4,4'-bpy Coordination Polymers", JACS Articles, vol. 124, 2002, 2568-2583.
Nugent, et al., "Enhancement of CO2 selectivity in a pillared pcu MOM platform through pillar substitution", ChemComm, The Royal Society of Chemistry, 2013, 1606-1608.

(56) References Cited

OTHER PUBLICATIONS

Nugent, et al., "Porous materials with optimal adsorption thermodynamics and kinetics for CO2 separation", Nature, Mar. 7, 2013, 80-84.

Park, et al., "Exceptional chemical and thermal stability of zeolitic imidazolate frameworks", PNAS, Jul. 5, 2006, 10186-10191.

Phan, et al., "Synthesis, Structure, and Carbon Dioxide Capture Properties of Zeolitic Imidazolate Frameworks", Accounts of Chemical Research, vol. 43, No. 1, Oct. 30, 2009, 58-67.

Shekhah, et al., "Made-to-order metal-organic frameworks for trace carbon dioxide removal and air capture", Nature Communications, Jun. 25, 2014, 1-7.

Siriwardane, et al., "Adsorption of CO2 on Molecular Sieves and Activated Carbon", Energy & Fuels, American Chemical Society, 2001, 279-284.

Skoulidas, et al., "Self-Diffusion and Transport Diffusion of Light Gases in Metal-Organic Framework Materials Assessed Using Molecular Dynamics Simulations", J. Phys. Chem., 2005, 15760-15768.

Subramanian, et al., "Porous Solids by Design: [Zn(4,4'-bpy)2(SiF6)]n-xDMF, a Single Framework Octahedral Coordination Polymer with Large Square Channels", Angew. Chem. Int. Ed. Engl., 1995, 2127-2129.

Uemura, et al., "Syntheses, Crystal Structures and Adsorption Properties of Ultramicroporous Coordination Polymers Constructed from Hexafluorosilicate Ions and Pyrazine", Eur. J. Inorg. Chem., 2009, 2329-2337.

Veawab, et al., "Corrosion Behavior of Carbon Steel in the CO2 Absorption Process Using Aqueous Amine Solutions", Ind. Eng. Chem. Res., 1999, 3917-3924.

Wang, et al., "Colossal cages in zeolitic imidazolate frameworks as selective carbon dioxide reservoirs", Nature Publishing Group, 2008, 207-212.

Yang, et al., "Computational Study of CO2 Storage in Metal-Organic Frameworks", American Chemical Society, 2008, 1562-1569.

Yang, et al., "Molecular Simulation of Separation of CO2 from Flue Gases in Cu—BTC Metal-Organic Framework", AIChE Journal, Nov. 2007, 2832-2840.

Yazaydin, et al., "Screening of metal-organic frameworks for carbon dioxide capture from flue gas using a combined experimental and modeling approach", J. Am. Chem. Soc. 131, 2009, 18198-18199.

US 10,328,380 B2

METAL ORGANIC FRAMEWORK ABSORBENT PLATFORMS FOR REMOVAL OF CO2 AND H2S FROM NATURAL GAS

CROSS-REFERENCE TO RELATED APPLICATIONS

This application claims priority to U.S. Provisional Application No. 62/144,175, filed 7 Apr. 2015, which application is incorporated herein by reference.

BACKGROUND

Today there is an increasing global desire to reduce greenhouse gas emissions and develop clean alternative vehicle fuels. Methane ($CH_4$), the primary component of natural gas (NG), is of particular interest as it is abundant and has lower carbon dioxide ($CO_2$) emission and more efficient combustion than other hydrocarbons due its high H/C ratio. Biogases, including landfill gas, are also seen as promising renewable energy resources, but, like NG, they contain significant amounts of water, $CO_2$, and hydrogen sulfide ($H_2S$) which must be removed before being transported, stored, and burned as a fuel. For example, NG must contain less than 1-2% $CO_2$ and 4 ppm $H_2S$ to meet fuel gas specifications for pipeline transportation. Within many industries, gas dehydration and removal of $CO_2$ and $H_2S$ remain some of the most intensive and challenging separations, in part due to the intolerance of many technologies to water.

Available technologies for refining NG and other biogases are often costly, multi-stage processes. Amine scrubbing is a common liquid phase system used to remove acid gases such as $CO_2$ and $H_2S$ from NG. However, stagnant historical operating efficiencies, and the excessive oxidative degradation, evaporation, and the corrosive nature of the alkanolamine aqueous solutions create a myriad of performance, safety, and environmental concerns. Solid, porous material systems, such as zeolite and metal organic frameworks (MOFs), offer more environmentally friendly alternatives for $CO_2$ capture, but require cumbersome, multi-stage processes. For example, zeolite has single-species selectivity for $CO_2$ and cyclic adsorption performance in the presence of moisture that require prior dehydration and $H_2S$ removal stages. MOFs, similarly, can be designed for $CO_2$ capture but exhibit prohibitively low selectivity for acid gases such as $H_2S$. Further, MOFs exhibit low selectivity and capture at low $CO_2$ partial pressures.

MOFs generally include porous crystals which are assembled from modular molecular building blocks, and provide a wide array of advantageous material properties, including high surface area, porosity, stability, and sorption potential. While the available building block options, and combinations thereof, are virtually limitless, such potential highlights the statistical difficulty in identifying and assembling MOFs with desired and particularized material properties and multi-faceted functionality. For example, many MOFs exhibit high selectivity towards a particular molecular species, but are highly intolerant to water and $H_2S$.

SUMMARY

In general, this disclosure describes porous metal organic frameworks (MOFs). In particular, this disclosure describes MOFs suitable for the capture and removal of gases and/or vapors from fluids. It should be noted that although the embodiments of this disclosure are described with respect to examples for gas capture, the embodiments described herein are generally applicable to many fields including gas molecule separation, gas storage, catalysis, sensors, drug delivery, rare gas separation, and proton conductivity.

In one embodiment, a method of capturing chemical species from a fluid composition comprises contacting a first metal organic framework characterized by the formula $[M_aM_b'F_{6-n}(O/H_2O)_w(\text{Ligand})_x(\text{solvent})_y]_z$ with a fluid composition comprising one or more of carbon dioxide, water, and hydrogen sulfide and capturing one or more of carbon dioxide, water, and hydrogen sulfide from the fluid composition.

The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

DETAILED DESCRIPTION

Figure 1A:
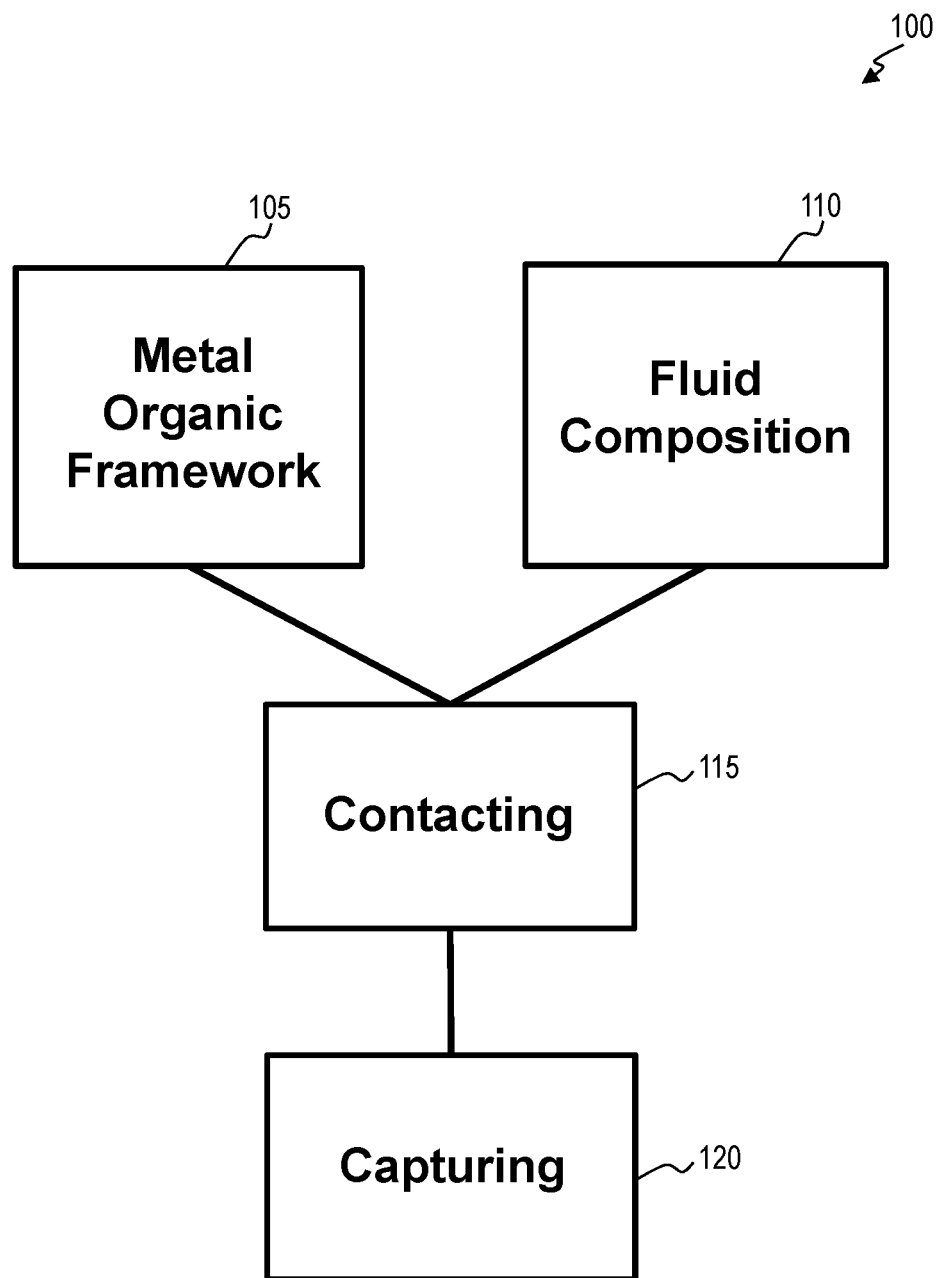
FIG. 1A illustrates a method for capturing one or more chemical species from a fluid composition via a metal organic framework, according to one or more embodiments of this disclosure.

Provided herein are a series of highly stable and highly tunable MOFs with high affinity and stability to water and $H_2S$. Such qualities allow for efficient and cost effective methods for dehydrating gases, vapors, and solvents capable of replacing many cumbersome and expensive industrial processes. Further, this novel series of MOFs can be designed with a variety of pore sizes and assembled with and without open-metal sites, affording tunable properties for a variety of separation applications. For example, the MOFs provided herein can capture chemical species from fluid compositions under conditions and in the presence of chemical species which render known gas capture technologies inefficient, impracticable, or inoperable. In particular, the MOFs provided herein can capture one or more of $H_2O$, $CO_2$ and $H_2S$ from a fluid composition, such as natural gas, while maintaining high structural integrity during both adsorption and desorption.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As used herein, "fluids" can refer to a gas, liquid, or combination thereof. A gas or liquid can include one or more components. For example, a fluid can include a gas stream comprising $CO_2$, $H_2S$ and water vapor.

As used herein, "refining" refers to removing one or more unwanted components or separating one or more components from remaining components of a composition, such as a fluid. For example, refining can include removing a fraction of $H_2S$ from a fluid, such as natural gas.

As used herein, "poly-functional" refers to the characteristic of having more than one reactive or binding sites. For example, a poly-functional ligand can attach to a metal ion in multiple ways, bridge multiple metal ions, or combinations thereof. Specifically, pyrazine is a poly-functional ligand.

Gas storage and separation using porous materials has experienced significant development in recent years in various industrial applications related to energy, environment, and medicine. Among porous materials, metal organic frameworks (MOFs) are a versatile and promising class of crystalline solid state materials which allow porosity and functionality to be tailored towards various applications. MOF crystal chemistry uses a molecular building block (MBB) approach that offers potential to construct MOFs where desired structural and geometrical information are incorporated into the building blocks prior to the assembly process.

Generally, MOFs comprise a network of nodes and ligands, wherein a node has a connectivity capability at three or more functional sites, and a ligand has a connectivity capability at two functional sites each of which connect to a node. Nodes are typically metal ions or metal containing clusters, and, in some instances, ligands with node connectivity capability at three or more functional sites can also be characterized as nodes. In some instances, ligands can include two functional sites capable of each connecting to a node, and one or more additional functional sites which do not connect to nodes within a particular framework. A MBB can comprise a metal-based node and an organic ligand which extrapolate to form a coordination network. Such coordination networks have advantageous crystalline and porous characteristics affecting structural integrity and interaction with foreign species (e.g., gases). The particular combination of nodes and ligands within a framework will dictate the framework topology and functionality. While essentially limitless combinations of nodes and ligands exist, to date, very few MOF materials are $H_2S$ stable which consequently preclude their use in gas separation.

As disclosed in co-owned U.S. Application No. 62/044,928, a series of isoreticular MOFs with periodically arrayed hexafluorosilicate ($SiF_6$) pillars, called SIFSIX-2-Cu-i and SIFSIX-3-Zn, SIFSIX-3-Cu and SIFSIX-3-Ni showed particularly high $CO_2$ selectivity and capture. These properties in SIFSIX-3-M materials suggest broad applications from ppm level $CO_2$ removal to bulk $CO_2$ separation. However, with the exception of SIFSIX-3-Ni, the SIFSIX-3-M materials were not tolerant to $H_2S$. And although these materials exhibit high structural structurally in the presence of $CO_2$, extensive exposure of all SIFSIX-3-M materials to moisture detrimentally induces a phase change and the formation of new 2D stable materials. These 2D materials exhibit relatively unaltered selectivity but diminished $CO_2$ uptake. This indicates that the SIFSIX-3-M materials series is not sufficiently robust to handle $CO_2$ and $H_2S$ capture in most critical applications throughout the oil and gas and renewable fuels industries, especially in applications which bring the materials into contact with moisture.

Provided herein are novel functionalized MOFs suitable for the removal of acid gases, particularly $CO_2$ and $H_2S$, which additionally exhibit high water vapor tolerance and stability over thousands of cycles. These MOFs eliminate the safety, efficiency, and environmental concerns associated with amine scrubbing techniques while providing high selectivity toward acid gases and negligible uptake of other components, including $CH_4$. The proposed class of materials will permit NG and biofuels refining approaches based on simultaneous removal of $CO_2$, $H_2S$ and water vapor. The benefits of this innovative approach include the following: (i) no environmental and safety hazards germane to amine scrubbing (ii) no preliminary separate desulfurization is necessary (iii) no separate gas drying is needed, and (iv) no compression-decompression/cooling of NG is required. Further, the MOFs provided herein offer exceptional thermal and mechanical stability, particularly during adsorption/desorption.

MOFs as provided herein comprise one or more MBBs. Generally, a MBB, or a network of MBBs, can be represented by the formula $[(node)_a(ligand)_b(solvent)_c]_n$, wherein n represents the number of molecular building blocks. Solvent represents a guest molecule occupying pores within the MOF, for example as a result of MOF synthesis, and can be evacuated after synthesis to provide a MOF with unoccupied pores. In one example, an evacuated MOF can be subsequently enriched with a guest molecule compatible with the MOF framework and/or pores for a particular purpose (e.g., to outfit the MOF for use as a sensor). In other embodiments, guest molecules can include adsorbed gases, such as $H_2S$. While guest molecules can impart functionality onto a MOF, such are not a permanent fixture of the MOF. Accordingly, the value of c can vary down to zero, without changing the definitional framework of the MOF. Therefore in many instances, MOFs as provided herein will be defined as $[(node)_a(ligand)_b]_n$, without reference to a solvent or guest molecule component.

In some embodiments herein, MOFs can be characterized by the formula $[(node)_a(ligand)_b(solvent)_c]_n$. A non-limiting list of solvents can include one or more of $H_2O$, DMF, and DEF. In some embodiments, solvent can include a chemical species present after fabrication of the MOF. In some embodiments, solvent can include a functionalizing guest molecule, such as water, DMF, and DEF. Some embodiments herein comprise a porous, uninhabited MOF characterized by the formula $[(node)_a(ligand)_b]_n$, wherein node comprises, generally, $M_aM_bF_xO_y(H_2O)_z$. In some embodiments, $M_a$ comprises elements selected from periodic groups IB, IIA, IIB, IIIA, IVA, IVB, VIB, VIIB, or VIII. In some embodiments, $M_b$ comprises elements selected from periodic groups IIIA, IIIB, IVB, VB, VIB, or VIII. In some embodiments, $M_a$ comprises elements selected from periodic groups IB, IIA, IIB, IIIA, IVA, IVB, VIB, VIIB, or VIII and $M_b$ comprises elements selected from periodic groups IIIA, IIIB, IVB, VB, VIB, or VIII. In some embodiments, $M_a$ can comprise one of the following cations: $Cu^{2-}$, $Zn^{2+}$, $Co^{2+}$, $Ni^{2+}$, $Mn^{2+}$, $Zr^{2+}$, $Fe^{2+}$, $Ca^{2+}$, $Ba^{2-}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+2}$, $Fe^{+3}$, $Cr^{2+}$, $Cr^{3+}$, $Ru^{2+}$, $Ru^{3+}$ and $Co^3$. In some embodiments, $M_b$ can be one of the following $Al^{+3}$, $Fe^{+2}$, $Fe^{+3}$, $Cr^{2+}$, $Cr^{3+}$, $Ti^{3+}$, $V^{3+}$, $V^{5-}$, $Sc^{3+}$, $In^{3+}$, $Nb^{5+}$, $Y^{3+}$. In some embodiments, $M_a$ can comprise one of the following cations: $Cu^{2-}$, $Zn^{2+}$, $Co^{2-}$, $Ni^{2+}$, $Mn^{2+}$, $Zr_{2+}$, $Fe^{2+}$, $Ca^{2+}$, $Ba^{2+}$, $Pb^{2+}$, $Pt^{2+}$, $Pd^{2+}$, $Ru^{2-}$, $Rh^{2+}$, $Cd^{2+}$, $Mg^{+2}$, $Al^{+3}$, $Fe^{+2}$, $Fe^{+3}$, $Cr^{2+}$, $Cr^{3+}$, $Ru^{2-}$, $Ru^{3+}$ and $Co^3$; $M_b$ can be one of the following $Al^{+3}$, $Fe^{+2}$, $Fe^{+3}$, $Cr^{2+}$, $Cr^{3+}$, $Ti^{3+}$, $V^{3+}$, $V^{5+}$, $Sc^{3+}$, $In^{3+}$, $Nb^{5+}$, $Y^{3+}$. In such embodiments, the ligand can be any bi-functional N-donnor linkers based on monocyclic or polycyclic group (aromatic or not).

In some embodiments, a ligand can comprise a polydentate, or poly-functional ligand, such as a bi-functional ligand, a tri-functional ligand, or ligands with four or more functional sites. In some embodiments, a ligand can comprise an N-donor linker. In some embodiments a ligand can comprise a poly-functional ligand. In some embodiments, a ligand can comprise a plurality of N-donor functional groups. In some embodiments, a ligand can comprise a monocyclic or polycyclic group structure, wherein the cyclic groups can be aromatic or non-aromatic. In some embodiments, a ligand can comprise a nitrogen-containing monocyclic or polycyclic group structure. In some embodiments, a ligand can comprise a nitrogen-containing heterocyclic ligand, including pyridine, pyrazine, pyrimidine, pyridazine, triazine, thiazole, oxazole, pyrrole, imidazole, pyrazole, triazole, oxadiazole, thiadiazole, quinoline, benzoxazole, benzimidazole, and tautomers thereof.

Some embodiments of suitable MOFs can be represented by the following general formula: $[M_aM_bF_x(O/H_2O)_z(Ligand)_2]_n$ wherein $M_a$ can be one of the following cations: $Cu^{2+}$, $Zn^{2+}$, $Co^{2+}$, $Ni^{2-}$, $Mn^{2+}$, $Zr^{2+}$, $Fe^{2+}$, $Ca^{2+}$, $Ba^{2+}$, $Pb^{2+}$, $Pt^{2+}$, $Pd^{2+}$, $Ru^{2+}$, $Rh^{2+}$, $Cd^{2+}$, $Mg^{+2}$, $Al^{+3}$, $Fe^{+2}$, $Fe^{+3}$, $Cr^{2+}$, $Cr^{3+}$, $Ru^{2+}$, $Ru^{3+}$ and $Co^3$; $M_b$ can be one of the following $Al^{+3}$, $Fe^{+2}$, $Fe^{+3}$, $Cr^{2+}$, $Cr^{3+}$, $Ti^{3+}$, $V^{3+}$, $V^{5+}$, $Sc^{3+}$, $In^{3+}$, $Nb^{5+}$, $Y^{3+}$; and the ligand can be any bi-functional N-donor linkers based on monocyclic or polycyclic group (aromatic or not).

The utility of MOFs such as those provided herein are highly dependent upon the framework's structural features such as structural strength, density, functionality, pore aperture dimensions, pore dimensions, the ratio of pore aperture dimensions to pore dimensions, pore accessibility, and the presence of a plurality of pore dimensions and/or pore aperture dimensions (e.g., a poly-porous MOF). The originality of this new class of crystalline porous materials is based, in part, on the fact that the shape of cavities, (i.e. square or rectangle based channels), is controlled from a structural point of view using appropriate cations and organic linkers. The novel MOF architectures disclosed herein offer a novel improvement on some MOF architectures by replacing silicon components with other metals, such as $Al^{3+}$, $Fe^{2+}$, $Fe^{3+}$, $V^{3+}$, $V^{4+}$, $V^{5+}$, $Nb^{5+}$, to afford highly stable materials with or without open metals sites. In some embodiments, the use of specific cations, such as $Al^{+3}$, $Fe^{+2}$, $Fe^{+3}$, $Cr^{2+}$, $Cr^{3+}$, $Ti^{3+}$, $V^{3+}$, $V^{5-}$, $Sc^{3+}$, $In^{3+}$, $Y^{3-}$, in $M_b$ site positions can introduce open-metal sites within the channels that enhance properties of gas capture.

These, and other features, collaborate to achieve MOFs with high affinity and stability to water and $H_2S$. Additionally, the novel series of MOFs structures disclosed herein can be designed with a variety of pore sizes and/or openmetal sites which afford tunable properties for a variety of gas/vapor/solvent separation applications. Tuning, in some embodiments, can include modification of the organic and/or inorganic components of the MOF. For example, lighter metal-based clusters can be used to lower the framework density and increase the relative wt. % of captured $CO_2$ and/or $H_2S$. Further, the MOF platforms as provided herein allow for an unprecedented high degree of tuning control at the molecular level, allowing the size and shape of channels within a MOF architecture to be rigorously controlled and adapted to specific separation of numerous gases, beyond $CO_2$ and $H_2S$.

In some embodiments, a representative $M_aM_bF_wO_x(H_2O)_y(Ligand)_z$ MOF structure can include a Ni $M_a$ constituent, an $M_b$ constituent group selected from one of Al, Fe, V, or Nb, and a Ligand comprising a pyrazine constituent group, wherein x can vary from 0 to 10. All such embodiments offer high affinity and stability to water vapor and $H_2S$, unlike the Cu and Zn-based analogues of SIFSIX-3-M materials made with Si. In some embodiments a MOF characterized by the formula $[M_aM_bF_{6-n}(O/H_2O)_n(Ligand)_2(solvent)_x]_n$, wherein $M_a$ equals Ni, $M_b$ equals Al, Fe, V or Nb, and ligand equals pyrazine, the pore size (channel size) of the resulting MOF can be about 3.3 Å to about 3.8 Å. In some embodiments, the channels are square/rectangular. In the same or in an alternative embodiment, a MOF can have a specific surface area of about 250 $m^2/g$ to about 500 $m^2/g$. In either of the same MOFs or in an alternative embodiment, a MOF can have a pore volume of about 0.1 $cm^3/g$ to about 0.25 $cm^3/g$. In a different embodiment, a more elongated ligand can provide an analogous MOF with much higher porosity.

FIG. 1A illustrates a method 100 for capturing 120 one or more chemical species from a fluid composition 110 via a first MOF 105. A method 100 for capturing 120 one or more chemical species from a fluid composition 110 can comprise contacting 115 a metal organic framework 105 characterized by the formula $[M_aM_bF_{6-n}(O/H_2O)_w(Ligand)_x(solvent)_y]_z$ with a fluid composition 110. Fluid composition 110 can comprise two or more chemical species. Fluid composition 110 can comprise natural gas. In one embodiment, fluid composition 110 comprises one or more of carbon dioxide, water, and hydrogen sulfide. In such an embodiment, fluid composition 110 can further comprise methane.

Method 100 can further comprise capturing 120 one or more chemical species from the fluid composition 110. Capturing 120 can comprise capturing one or more of carbon dioxide, water, and hydrogen sulfide. Capturing 120 can comprise capturing two or more of carbon dioxide, water, and hydrogen sulfide. In some embodiments, capturing 120 comprises physical adsorption of the one or more captured chemical species by the first MOF 105. In some embodiments, capturing 120 comprises chemisorption of the one or more captured chemical species by the first MOF 105. Chemisorption can occur by one or more captured chemical species chemically interacting with one or more open metal sites of the first MOF 105. In other embodiments, capturing 120 comprises physical adsorption and chemisorption of the one or more captured chemical species by the metal organic framework. Capturing 120 can comprise wholly or partially containing a chemical species within a pore of a MOF. In some embodiments, capturing 120 consists of chemisorption. In some embodiments, capturing 120 consists of physical adsorption. Capturing 120 can occur in a capturing environment. A capturing environment can comprise one or more of ambient temperature or pressure. A capturing environment can comprise a pressurize-controlled vessel. A capturing environment can comprise a temperature-controlled vessel. A capturing environment can comprise a pressure and temperature-controlled vessel. A capturing environment can comprise the first MOF 105 in the form of a fixed bed, a packed column, or combinations thereof.

Capturing 120 can further comprise changing the temperature of the capture environment to alter the affinity of one or more chemical species for the MOF. Similarly, capturing 120 can further comprise changing the pressure of the capture environment to alter the affinity of one or more chemical species for the MOF. Additionally, capturing 120 can further comprise changing the temperature and pressure of the capture environment to alter the affinity of one or more chemical species for the MOF. In such embodiments, the chemical species can particularly include carbon dioxide, water, and hydrogen sulfide.

Method 100 can further comprise desorbing one or more of carbon dioxide, water, and hydrogen sulfide from the MOF. Method 100 can further comprise desorbing two or more of carbon dioxide, water, and hydrogen sulfide from the MOF. Desorbing can occur in a desorbing environment. A desorbing environment can comprise one or more of ambient temperature or pressure. A desorbing environment can comprise a pressurize-controlled vessel. A desorbing environment can comprise a temperature-controlled vessel. A desorbing environment can comprise a pressure and temperature-controlled vessel. While a MOF can capably capture a number of gaseous or vapor phase species, a relative affinity hierarchy will, in principle, exist among those species. In embodiments where method 100 comprises desorbing two or more of carbon dioxide, water, and hydrogen sulfide from the MOF, carbon dioxide, water, and hydrogen sulfide can be sequentially desorbed in descending order of affinity. In a particular embodiment, $H_2S$ is desorbed first, $CO_2$ is desorbed second, and $H_2O$ is desorbed last.

In some embodiments, the relative affinity hierarchy of chemical species can be manipulated. Accordingly, desorbing can further comprise changing the temperature of the desorbing environment to alter the affinity of one or more chemical species for the MOF. Similarly, desorbing can further comprise changing the pressure of the desorbing environment to alter the affinity of one or more chemical species for the MOF. Additionally, desorbing can further comprise changing the temperature and pressure of the desorbing environment to alter the affinity of one or more chemical species for the MOF. In such embodiments, the chemical species can particularly include carbon dioxide, water, and hydrogen sulfide. In some embodiments, one or more of capturing and desorbing is effected by multicolumn pressure-temperature swing adsorption. Multicolumn pressure-temperature swing adsorption is known in the art.

Method 100 can further comprise contacting 115 the fluid composition 110 with a second MOF, characterized by the formula $[M_cM_dF_{6-n}(O/H_2O)_w(Ligand)_x(solvent)_y]_z$. In some embodiments, the second MOF is different from the first MOF 105. In some embodiments, contacting 115 the fluid composition with the first MOF 105 and the second MOF occurs separately. In some embodiments, contacting 115 the fluid composition with the first MOF 105 and the second MOF occurs sequentially. In some embodiments, contacting 115 the fluid composition with the first MOF 105 and the second MOF occurs simultaneously. Method 100 can further comprise contacting 115 the fluid composition 110 with three or more MOFs.

In some embodiments, the first MOF comprises one or more MOFs as provided herein. For example, the first MOF can comprise an MOF characterized by the formula [NiNbF$_{6-n}$(O/H$_2$O)$_w$(Ligand)$_x$(solvent)$_y$]$_z$. In some embodiments the second MOF comprises one or more MOFs as provided herein. For example, the second MOF can comprise an MOF characterized by the formula [NiM$_d$F$_{6-n}$(O/H$_2$O)$_w$(Ligand)$_x$(solvent)$_y$]$_z$ wherein M$_d$ comprises Al$^{+3}$, Fe$^{+2}$, or Fe$^{+3}$ In some embodiments, the MOF is characterized by the formula [NiNbF$_{6-n}$(O/H$_2$O)$_w$(Ligand)$_x$(solvent)$_y$]$_z$ and the second MOF is characterized by the formula [NiM$_d$F$_{6-n}$(O/H$_2$O)$_w$(Ligand)$_x$(solvent)$_y$]$_z$ wherein M$_d$ comprises Al$^{+3}$, Fe$^{+2}$, or Fe$^{+3}$.

Figure 1B:
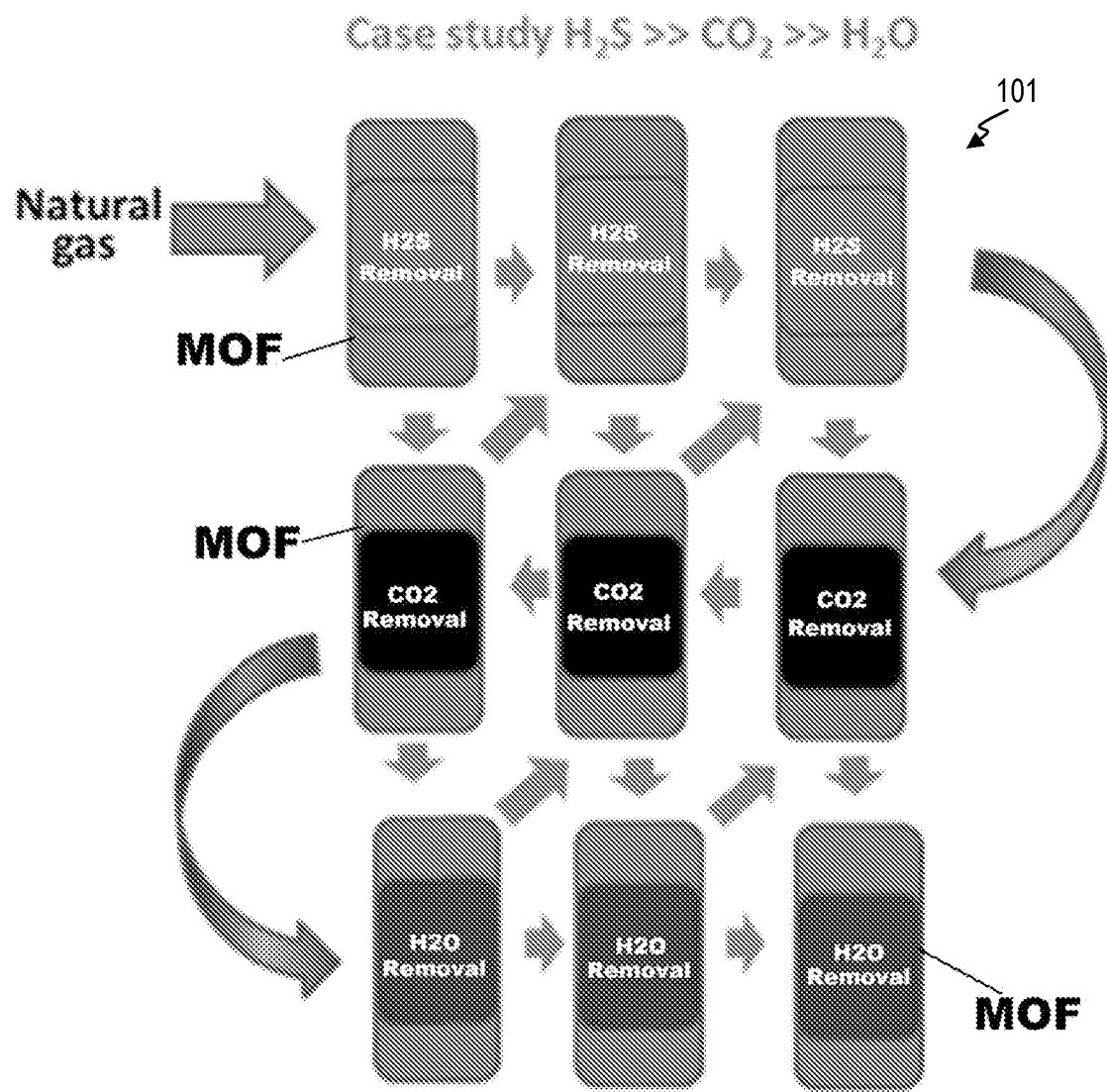
FIG. 1B illustrates a multicolumn pressure-temperature swing adsorption (PTSA) method for capturing one or more chemical species from a fluid composition via a metal organic framework, according to one or more embodiments of this disclosure.

FIG. 1B illustrates a method 101 for removing one or more of carbon dioxide, water, and hydrogen sulfide from natural gas via a MOF. Removing can one or more of carbon dioxide, water, and hydrogen sulfide from natural gas can occur simultaneously. Removing can one or more of carbon dioxide, water, and hydrogen sulfide from natural gas can occur separately. Removing can occur in a multicolumn pressure-temperature swing adsorption (PTSA) system. In one embodiment, the MOF comprises one of Ni(Al/Fe/V/Nb)F$_5$(O/H$_2$O)$_x$(pyrazine)$_2$(solvent)$_x$. In another embodiment, the MOF comprises two or more of Ni(Al/Fe/V/Nb)F$_5$(O/H$_2$O)$_x$(pyrazine)$_2$(solvent)$_x$.

Figure 2:
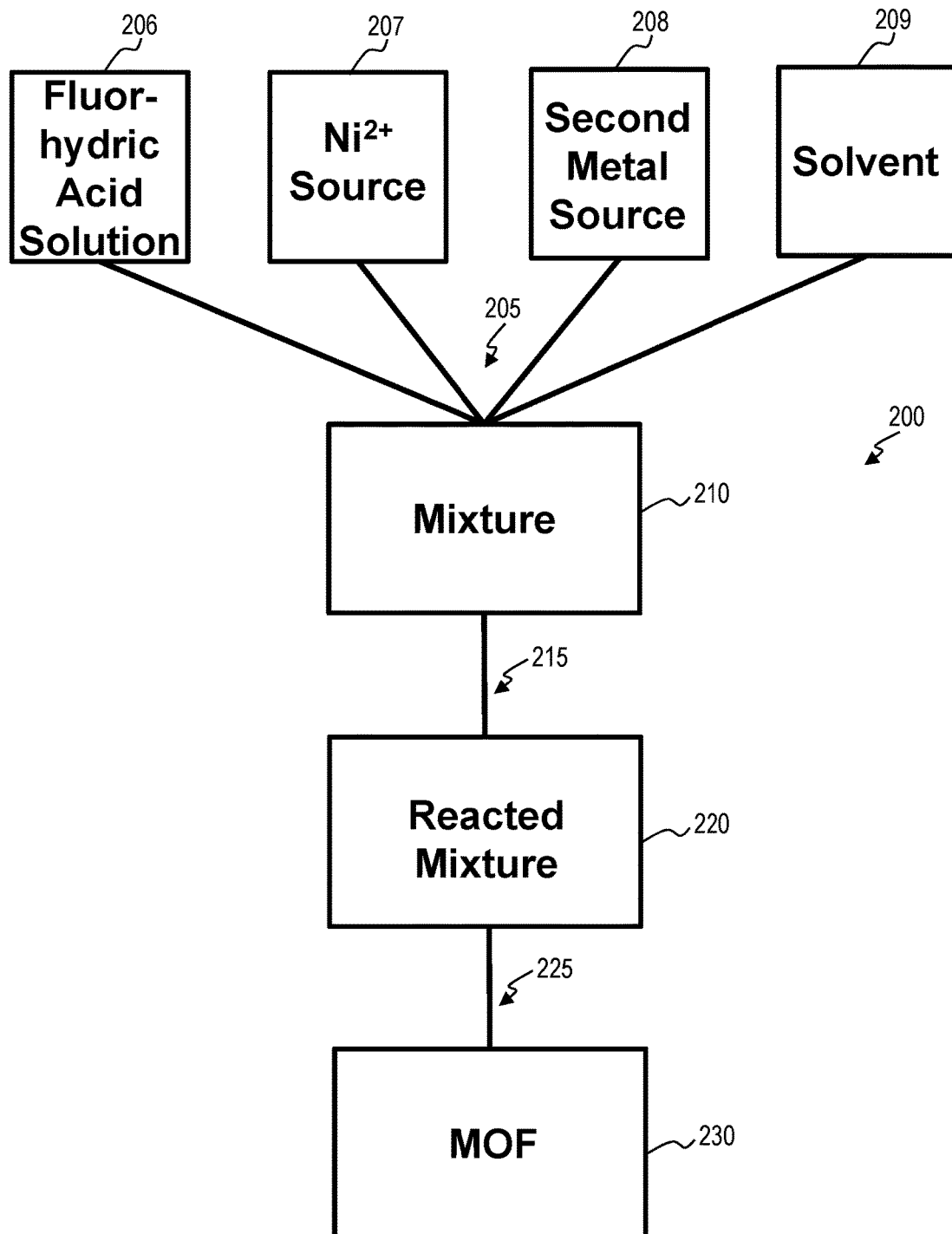
FIG. 2 illustrates a method of fabricating a metal organic framework, according to one or more embodiments of the disclosure.

MOFs as provided herein can be fabricated using a solvo(hydro)thermal synthetic procedure. As shown in FIG. 2, a method for fabricating 200 a MOF 230 can include combining 205 reactants. Reactants can include one or more of a fluorhydric acid solution 206 with a Ni$^{2+}$ source 207, a second metal source 208, and a solvent 209 to form a mixture 210. A Ni$^{2+}$ source 207 can include one or more of nickel nitrate, hydrated nickel nitrate, nickel chloride, hydrated nickel chloride, nickel fluoride, hydrated nickel fluoride, nickel oxide, or hydrated nickel oxide. The second metal source 208 can include an Al$^{+3}$ source, an Fe$^{-2}$ source, an Fe$^{+3}$ source, a Cr$^{2+}$ source, a Cr$^{3+}$ source, a Ti$^{3+}$ source, a V$^{3+}$ source, a V$^{5+}$ source, a Sc$^{3+}$ source, an In$^{3+}$ source, a Nb$^{5+}$ source, or a Y$^{3+}$ source, for example. These, metals can be in the form of nitrates, hydrated nitrates, chlorides, hydrated chlorides, fluorides, hydrated fluorides, oxides, hydrated oxides, and combinations thereof. The solvent 209 can include one or more of H$_2$O, dimethylformamide (DMF), and diethylformamide (DEF).

The method for fabricating 200 can further comprise to reacting 215 the mixture 210, sufficient to form a reacted mixture 220. Reacting 215 can include contacting the fluorhydric acid solution 206, the Ni$^{2+}$ source 207, the second metal source 208, and the solvent 209. Reacting 215 can further comprise stirring or agitating the mixture 210, or heating the mixture 210. Heating the mixture 210 can comprise heating to a temperature between about 80° C. to about 200° C. The reacted mixture 220 can be further processed 225 to provide a fabricated MOF 230. Processing 220 can include one or more of filtering the reacted mixture 220, rinsing the reacted mixture 220 with water, removing excess reactants from the reacted mixture 220. In some embodiments, guest molecules are optionally evacuated from a fabricated MOF 230. Guest molecules can include solvent guest molecules, or derivatives thereof.

Figure 3B:
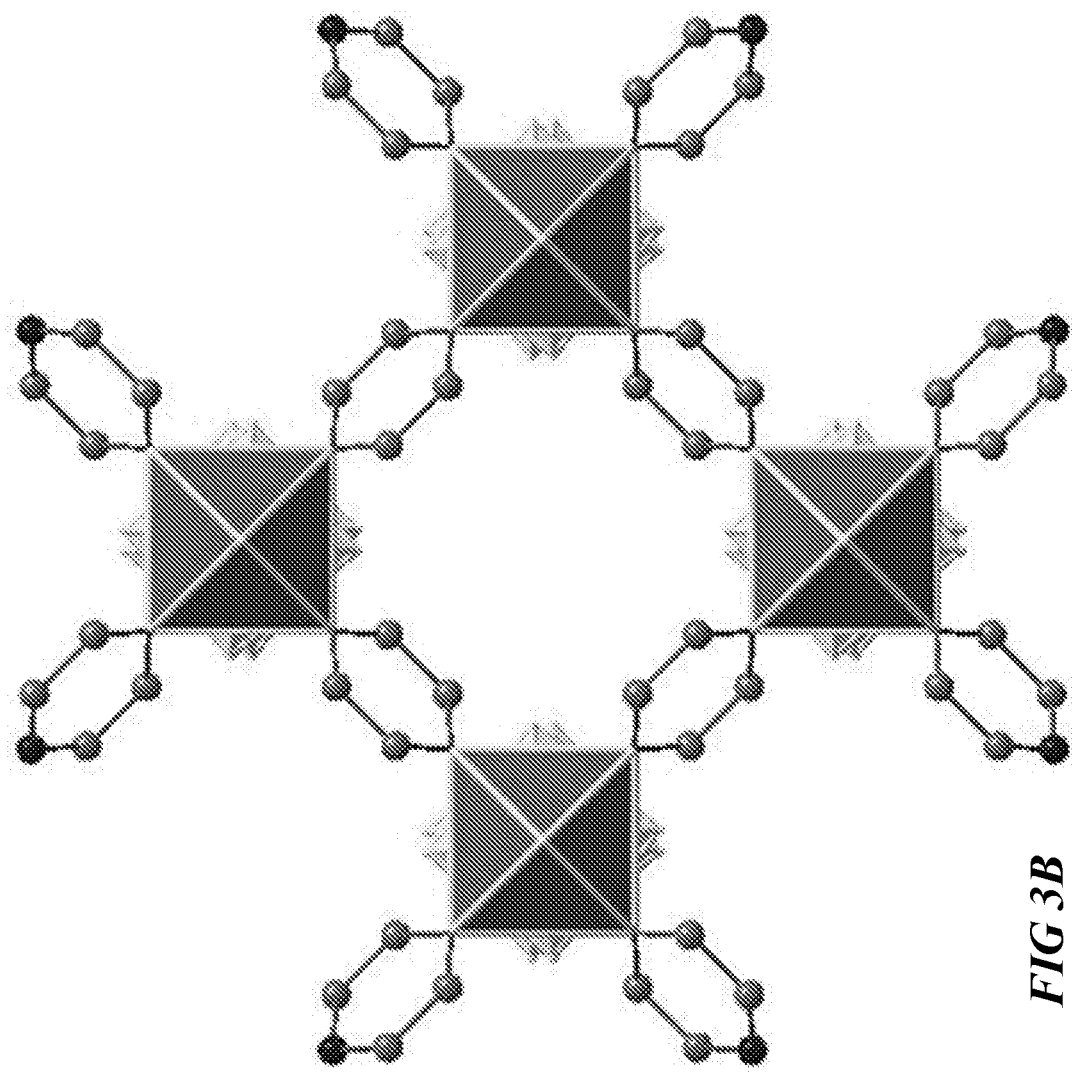
FIG. 3B illustrates a schematic view of a metal organic framework, according to one or more embodiments of this disclosure.
Figure 3A:
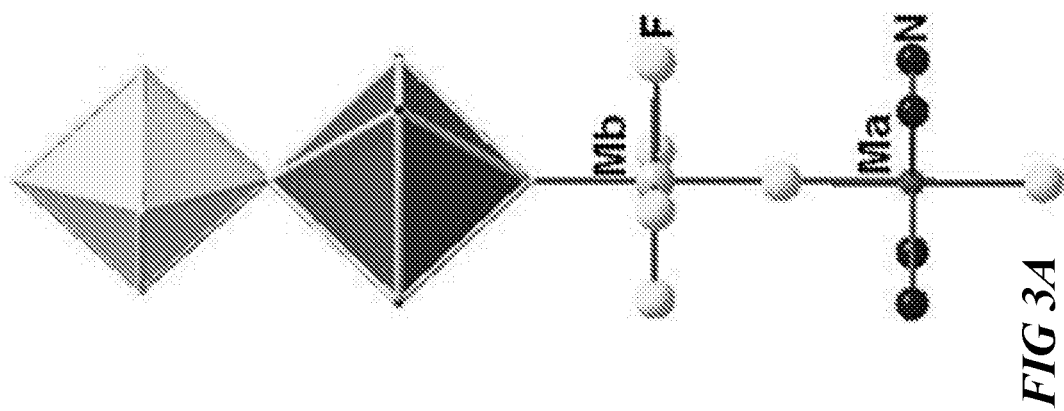
FIG. 3A illustrates a schematic of an inorganic chain, according to one or more embodiments of this disclosure.

One MOF synthesis strategy provided herein comprises linking inorganic chains using appropriate N-donor based linkers to deliberately generate channels along one crystallographic direction. The inorganic chains are built up from the trans-connection between M$_a$N$_4$F$_2$ and M$_b$F$_4$(H$_2$O)$_2$ octahedra or between M$_a$N$_4$F$_2$ and M$_b$F$_5$(H$_2$O) octahedra or between M$_a$N$_4$F$_2$ octahedra and M$_b$F$_5$(O) octahedra. FIG. 3A illustrates an example of an inorganic chain, built up from M$_a$N$_4$F$_2$ and M$_b$F$_5$(H$_2$O) octahedra. The resulted inorganic chains are linked to each other using bi-functional N-donor organic ligands, thereby generating channels with different sizes and shapes depending on the nature of the organic linker. FIG. 3B illustrates a schematic view of one embodiment of a MOF comprising a NiNbF$_5$O(pyrazine)$_2$ structure, viewed along the c-axis.

Figure 4A:
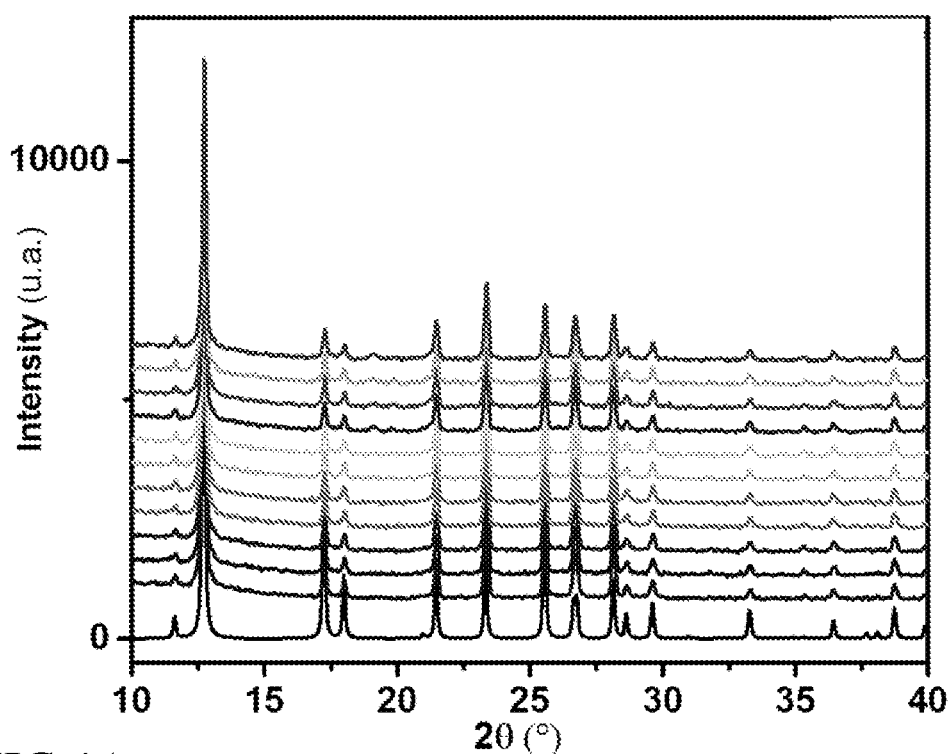
FIG. 4A illustrates powder X-ray diffraction data of a metal organic framework, according to one or more embodiments of this disclosure.
Figure 4B:
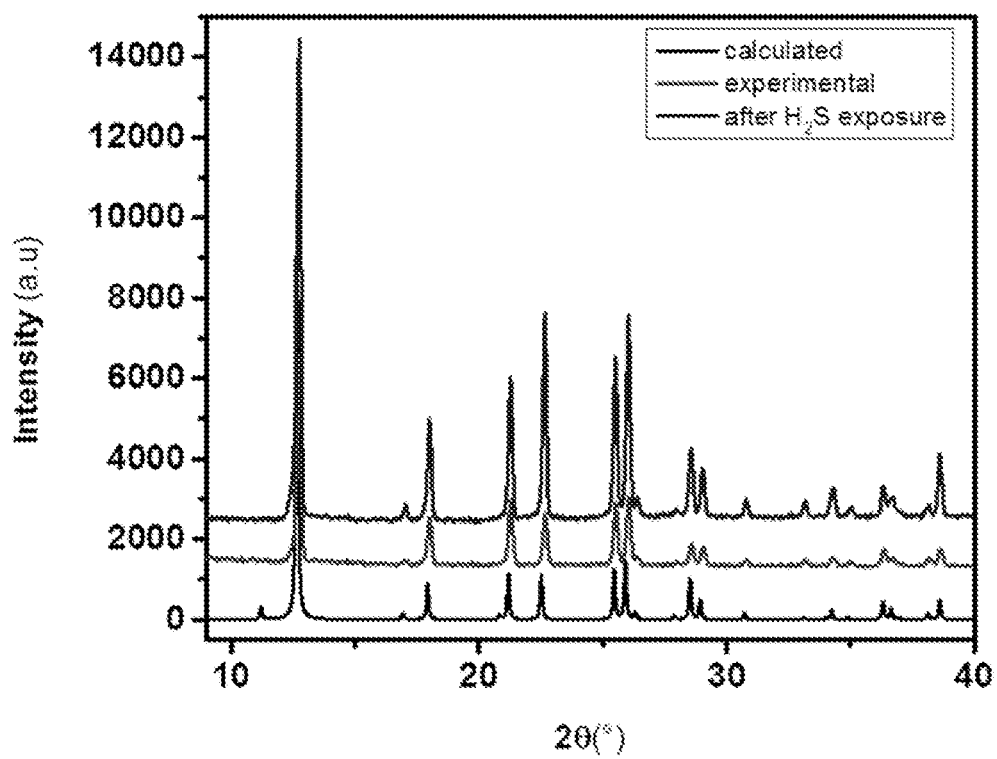
FIG. 4B illustrates powder X-ray diffraction data of a metal organic framework, according to one or more embodiments of this disclosure.

In one embodiment, a representative M$_a$M$_b$F$_x$O$_y$(Ligand)$_2$ MOF structure can include a Ni M$_a$ constituent, a Nb M$_b$ constituent group, and a Ligand comprising a pyrazine constituent group. FIG. 4A illustrates powder X-ray diffraction data of this MOF, characterized by the formula NiNbF$_5$O(pyrazine)$_2$(solvent)$_x$, confirming the high stability of the MOF in the presence of water. FIG. 4B illustrates powder X-ray diffraction data of this MOF, confirming the high stability of the MOF in the presence of H$_2$S.

Figure 5A:
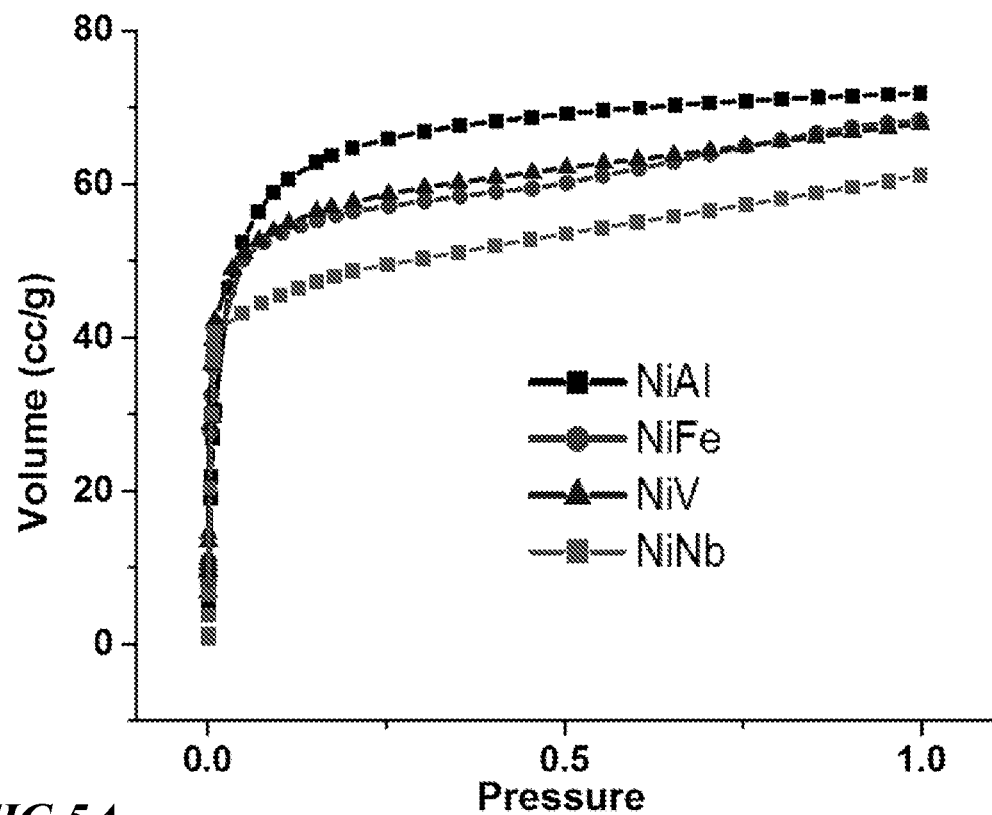
FIG. 5A illustrates isotherm data for various metal organic frameworks, according to one or more embodiments of this disclosure.
Figure 5B:
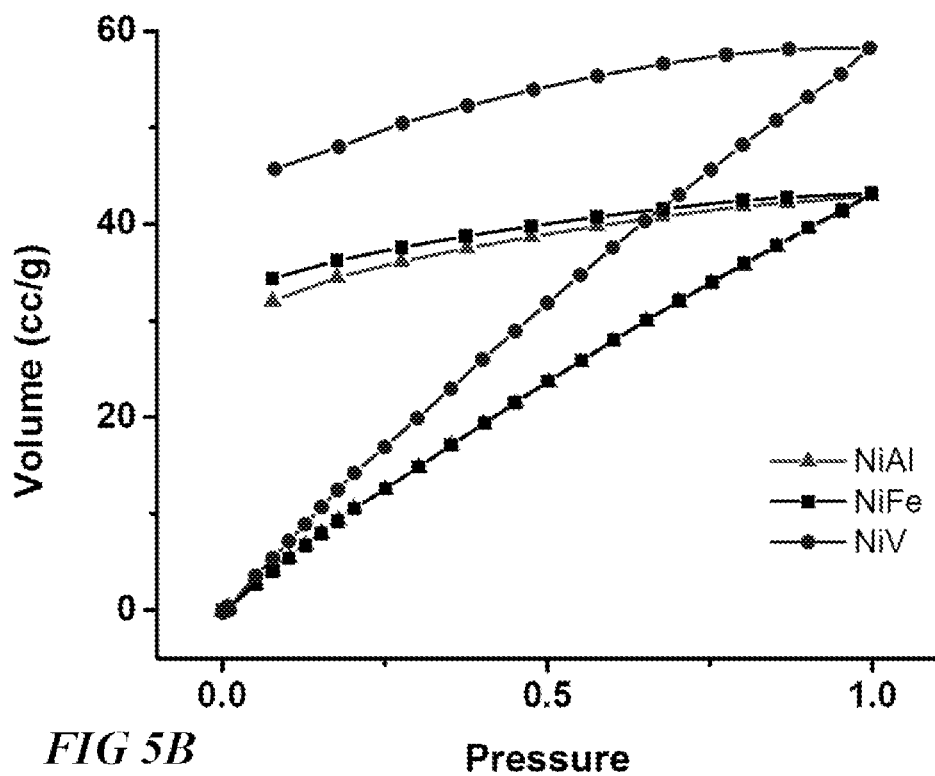
FIG. 5B illustrates isotherm data for various metal organic frameworks, according to one or more embodiments of this disclosure.
Figure 5C:
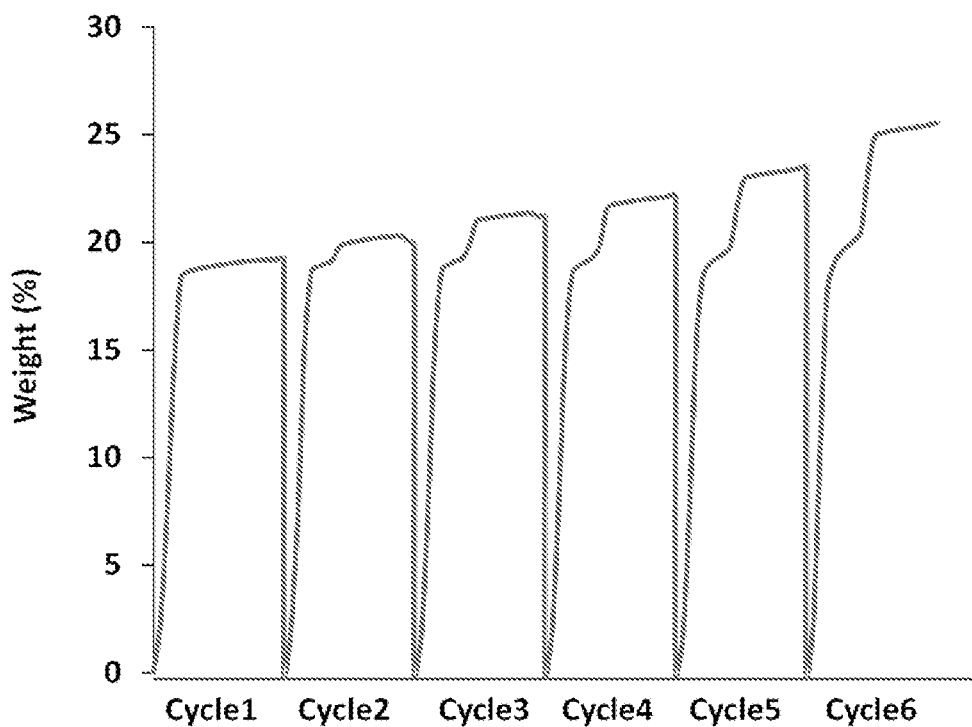
FIG. 5C illustrates isotherm data for a metal organic framework, according to one or more embodiments of this disclosure.

FIGS. 5A-C illustrates the broad potential for MOFs characterized by the formula Ni(Al/Fe/V/Nb)F$_5$(O/H$_2$O)$_x$(pyrazine)$_2$(solvent)$_x$, and variants thereof. FIG. 5A illustrates CO$_2$ isotherms at 298 K for each of these four MOFs, which show extremely high sorption of CO$_2$ across all test pressures (0-1 bar), FIG. 5B illustrates H$_2$S isotherms at 298K for three MOFs characterized by the formula Ni(Al/Fe/V)F$_5$(O/H$_2$O)$_x$(pyrazine)$_2$(solvent)$_z$, which shows across all test pressures (0-1, wherein 1 corresponds to a 0.1 H$_2$S partial pressure).

FIG. 5C Illustrates H$_2$O sorption isotherms at 298K for Ni(Al)F$_5$(O/H$_2$O)$_x$(pyrazine)$_2$(solvent)$_z$, indicating the high suitability of this MOF for gas dehydration applications, among others. These results demonstrate the value of the MOF embodiment characterized by the formula Ni(Al/Fe/V/Nb)F$_5$(O/H$_2$O)$_x$(pyrazine)$_2$(solvent)$_x$ as a platform for refining a number of valuable hydrocarbon gases and fluids, including methane, natural gas, and biogas. The exemplary performance and properties of the Nb$^{5+}$ based MOFs disclosed herein are notably achieved in spite of having no open metal sites. These and other results can be expected in similar other embodiments, with or without open metal sites, such as MOF structure characterized by the formula NiM$_b$F$_5$O(pyrazine)$_2$, wherein M$_b$ can be one of the following Al$^{+3}$, Fe$^{-2}$, Fe$^{+3}$, Cr$^{2+}$, Cr$^{3+}$, Ti$^{3+}$, V$^{3+}$, V$^{5+}$, SC$^{3+}$, In$^{3+}$, Nb$^{5+}$, Y$^{3+}$. These and other results can be expected in similar other embodiments, with or without open metal sites, such as MOF structure characterized by the formula M$_a$NbF$_5$O(pyrazine)$_2$, wherein M$_a$ can be one of the following cations: Cu$^{2+}$, Zn$^{2+}$, Co$^{2+}$, Ni$^{2+}$, Mn$^{2+}$, Zr$^{2+}$, Fe$^{2+}$, Ca$^{2+}$, Ba$^{2+}$, Pb$^{2+}$, Pt$^{2+}$, Pd$^{2+}$, Ru$^{2+}$, Rh$^{2+}$, Cd$^{2+}$, Mg$^{+2}$, Al$^{+3}$, Fe$^{+2}$, Fe$^{+3}$, Cr$^{2+}$, Cr$^{3+}$, Ru$^{2+}$, Ru$^{3+}$. These and other results can also be expected in similar other embodiments, with or without open metal sites, such as MOF structure characterized by the formula M$_a$(Al/Fe/V)F$_5$O(pyrazine)$_2$, wherein M$_a$ can be one of the following cations: Cu$^{2+}$, Zn$^{2+}$, Co$^{2+}$, Ni$^{2+}$, Mn$^{2+}$, Zr$^{2+}$, Fe$^{2+}$, Ca$^{2+}$, Ba$^{2+}$, Pb$^{2+}$, Pt$^{2+}$, Pd$^{2+}$, Ru$^{2+}$, Rh$^{2+}$, Cd$^{2+}$, Mg$^{+2}$, Al$^{+3}$, Fe$^{+2}$, Fe$^{+3}$, Cr$^{2+}$, Cr$^{3+}$, Ru$^{2-}$, Ru$^{3+}$.

Example 1

Figure 6:
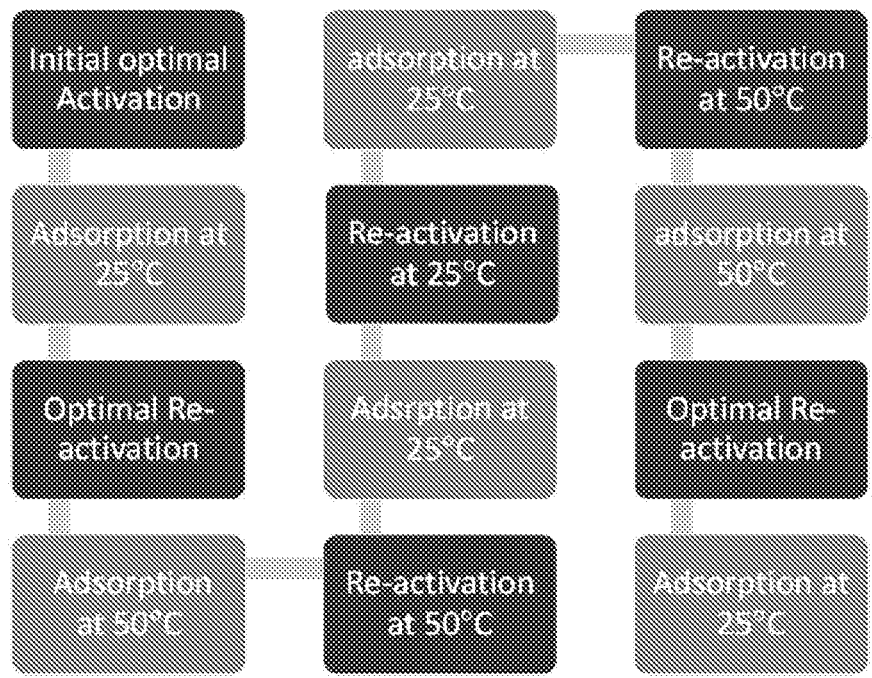
FIG. 6 illustrates a block flow diagram of sequence of tests for adsorption column breakthrough studies to evaluate the performances of the materials in temperature swing cyclic (TSR) and vacuum swing regeneration (VSR) modes using CO2/$H_2S$/CH4:5/5/90 mixture, according to one or more embodiments of this disclosure.

In order to study the performance of $NiAlF_5O(pyrazine)_2$ for adsorption of $CO_2$ and $H_2S$, a series of cyclables testing were carried out in a flow mode system using the sequence of tests described in FIG. 6.

Figure 7:
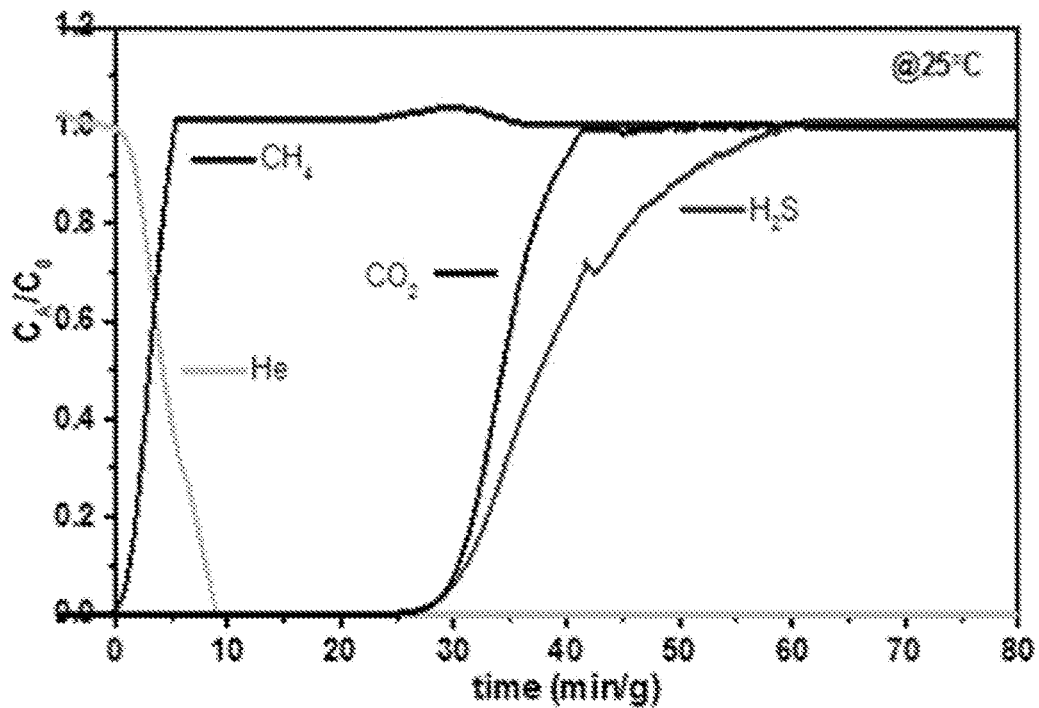
FIG. 7 illustrates a graphical view of column breakthrough test of $CO_2/H_2S/CH_4$ with 10 $cm^3$/min flow rate on $NiAlF_5O(\text{pyrazine})_2$ at 25° C. (1 bar) using TSR mode, according to one or more embodiments of this disclosure.

$NiAlF_5O(pyrazine)_2$, a material from a related $SiF_6$ platform which is known to be very selective to $CO_2$ was tested. Interestingly, the gas adsorption testings using $CO_2/H_2S/CH_4$:5/5/90 at 25° C. in TSR mode showed a retention time in the column of 27 min/g for $H_2S$ and $CO_2$, respectively (FIG. 7), indicative of similar affinity of the $NiAlF_5O$ $(pyrazine)_2$ framework to both $CO_2$ and $H_2S$. These results showed that $H_2S$ and $CO_2$ could be removed simultaneously with the same affinity.

Figure 8:
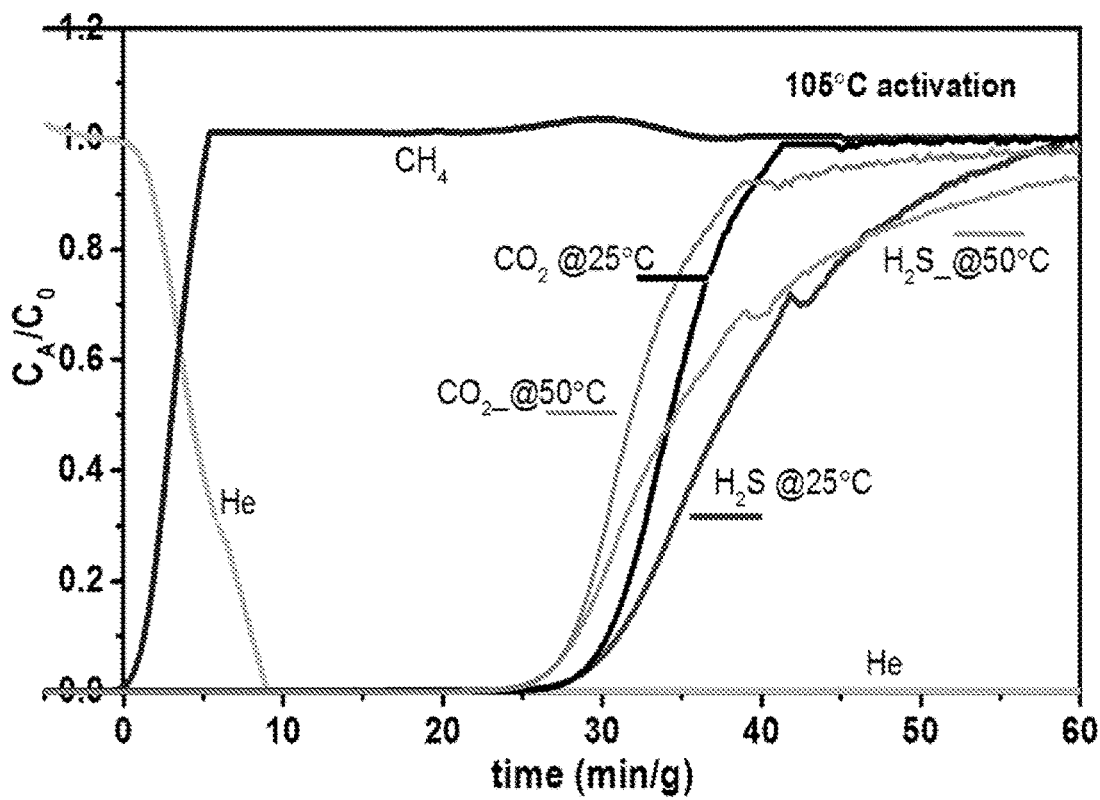
FIG. 8 illustrates a graphical view of column breakthrough tests of $CO_2/H_2S/CH_4$ with 10 $cm^3$/min flow rate on $NiAlF_5O(\text{pyrazine})_2$ at 25° C. and 50° C. (1 bar) respectively (effect of adsorption temperature on retention time), according to one or more embodiments of this disclosure.

Most importantly, heating the adsorption column in a second TSR (temperature swing regeneration mode) cycle to 50° C. for $NiAlF_5O(pyrazine)_2$ did not significantly affect the retention time (25 vs 27 min/g) for both $H_2S$ and $CO_2$ respectively (FIG. 8).

Figure 9:
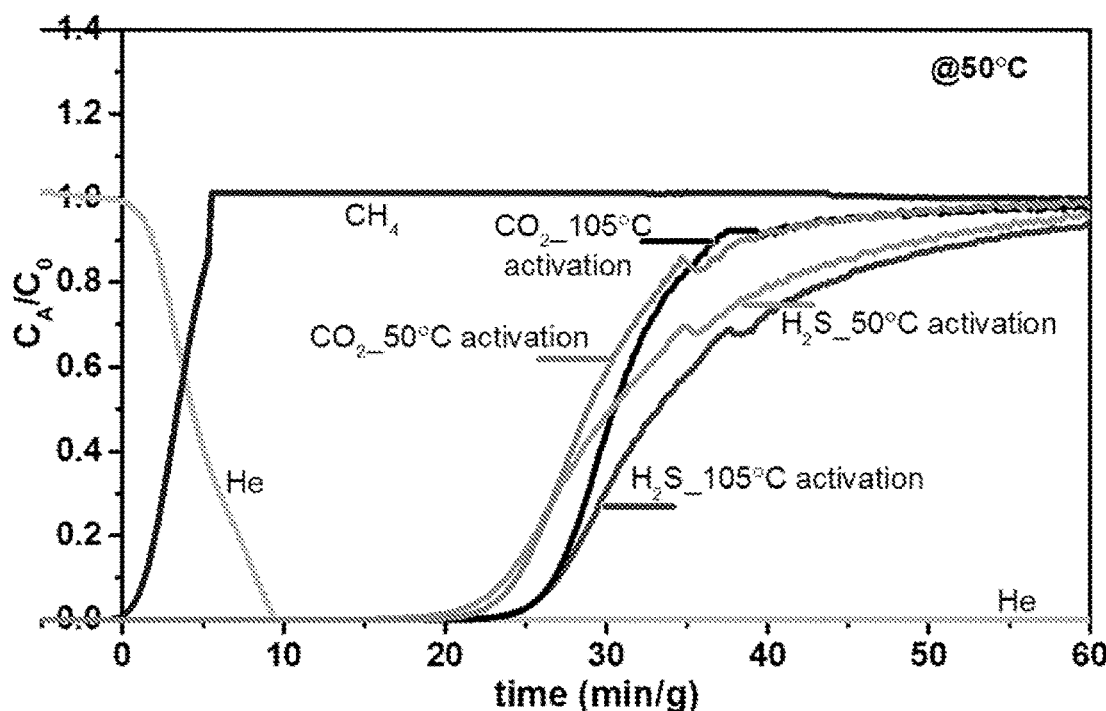
FIG. 9 illustrates a graphical view of column breakthrough tests of $CO_2/H_2S/CH_4$ with 10 cm$^3$/min flow rate on NiAlF$_5$O(pyrazine)$_2$ at 50° C. (1 bar) after activation at different temperatures (effect of adsorption temperature on retention time of different gases), confirming the recyclability of the material, according to one or more embodiments of this disclosure.

FIG. 9 shows that TSR mode could be practiced for $NiAlF_5O(pyrazine)_2$ using reactivation at 50° C. and even VSR mode at 25° C. with a minimum loss in the $H_2S$ retention time while keeping the same affinity for $H_2S$ and $CO_2$. FIG. 9 shows that for $NiAlF_5O(pyrazine)_2$, the $H_2S$ and $CO_2$ uptakes were reduced by 20% between TSR and VSR (vacuum swing regeneration) mode when adsorption is carried at 50° C.

Finally, the reproducibility test (6th cycle) after 5 adsorption-desorption tests showed that $NiAlF_5O(pyrazine)_2$ exhibit a reproducible $H_2S$ and $CO_2$ adsorption performance. In this case, $NiAlF_5O(pyrazine)_2$ can be utilized as a potential material for the simultaneous removal of $H_2S$ and $CO_2$.

Example 2

Figure 10:
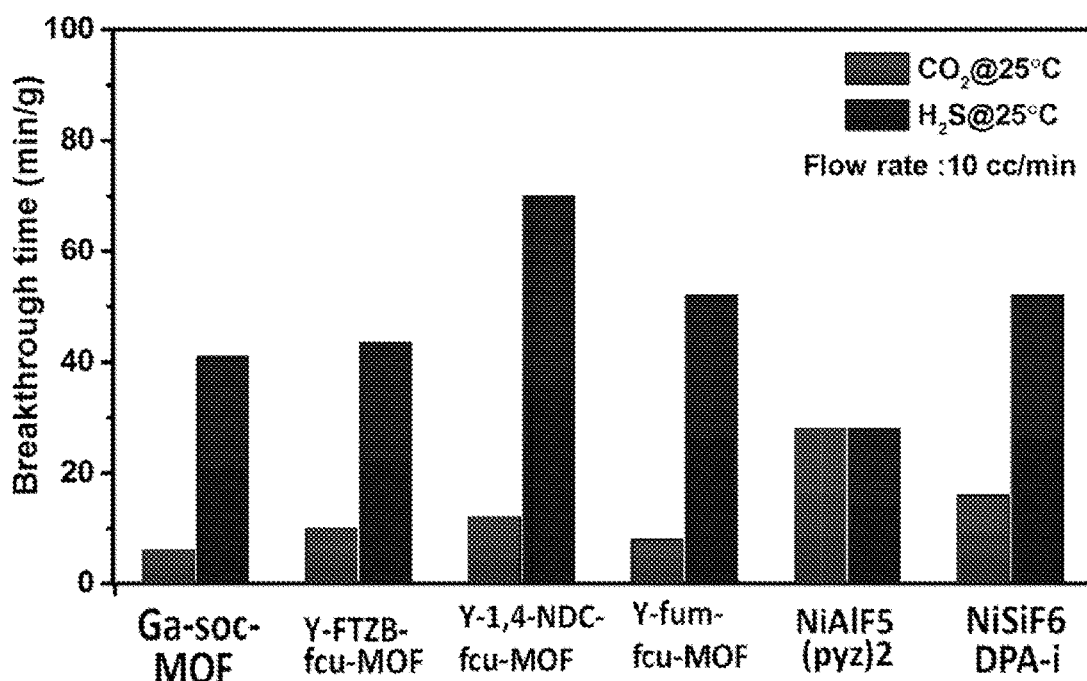
FIG. 10 illustrates a graphical view of comparison of retention time of $CO_2$ and $H_2S$ for studied materials during column breakthrough tests at 25° C. (1 bar) after optimal activation of the samples (gas mixture $CO_2/H_2S/CH_4$ (5/5/90) with 10 cm$^3$/min flow rate was used for the experiments), according to one or more embodiments of this disclosure.
Figure 13:
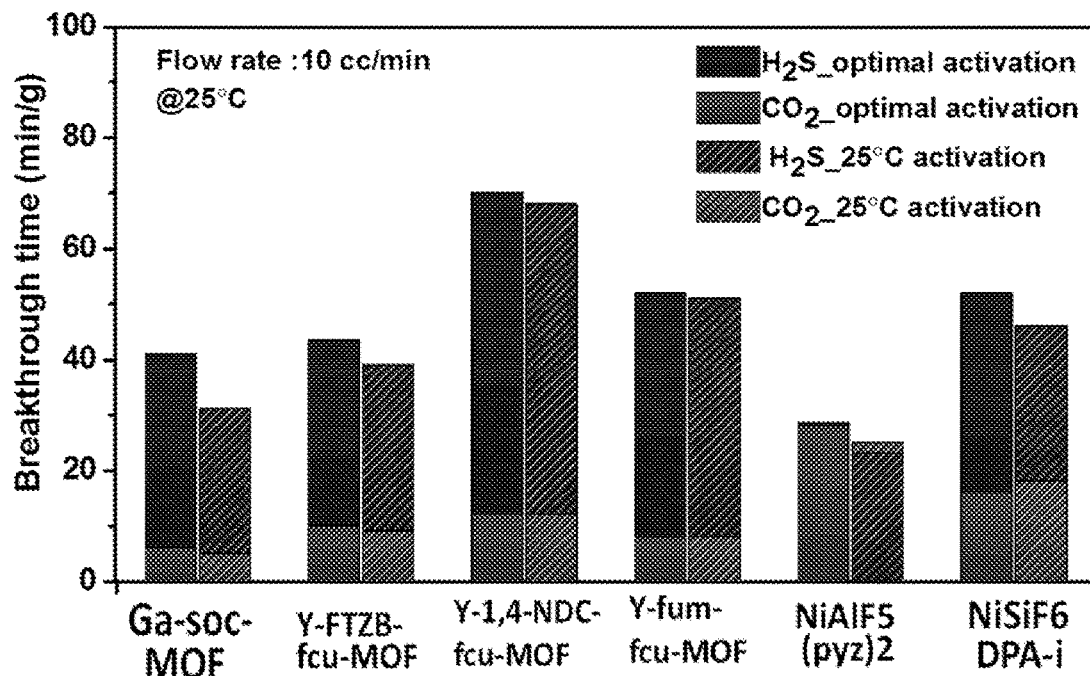
FIG. 13 illustrates a graphical view of comparison of retention time of $CO_2$ and $H_2S$ for studied materials during column breakthrough tests at 25° C. after optimal activation and 25° C. activation of the samples respectively (gas mixture $CO_2/H_2S/CH_4$ (5/5/90) with 10 cm$^3$/min flow rate was used for the experiments) and comparison describes compatibility of the studied materials for Vacuum Swing Regeneration (VSR) at 25° C., according to one or more embodiments of this disclosure.
Figure 14:
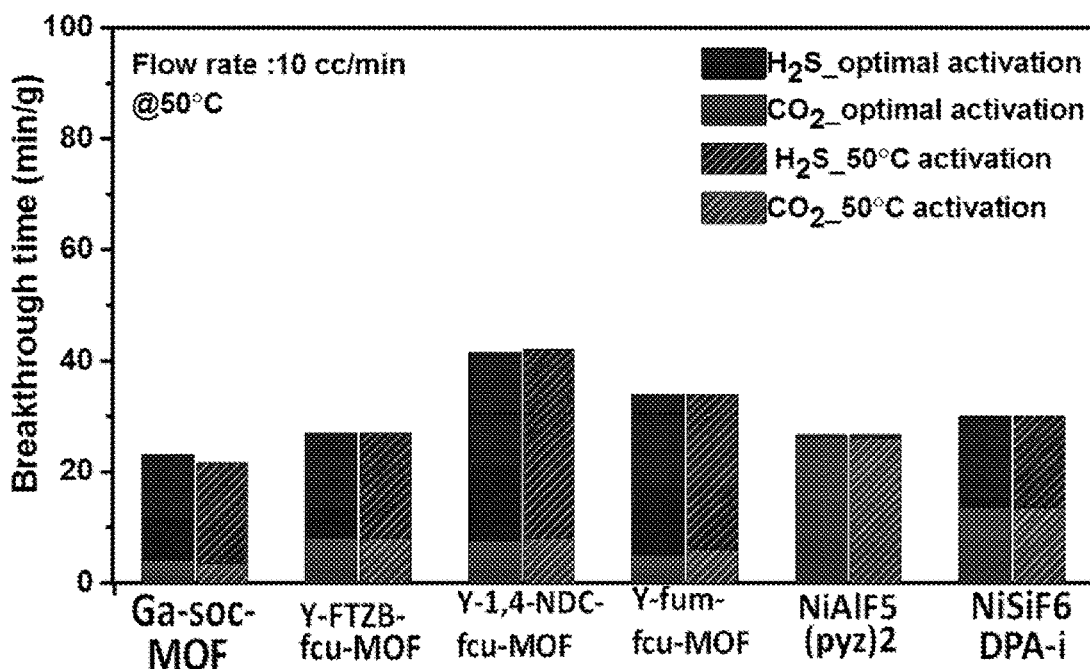
FIG. 14 illustrates a graphical view of comparison of retention time of $CO_2$ and $H_2S$ for studied materials during column breakthrough tests at 50° C. after optimal activation and 50° C. activation of the samples respectively (gas mixture $CO_2/H_2S/CH_4$ (5/5/90) with 10 cm$^3$/min flow rate was used for the experiments) and comparison describes compatibility of the studied materials for Vacuum Swing Regeneration (VSR) at 50° C., according to one or more embodiments of this disclosure.

With the exception of $NiAlF_5O(pyrazine)_2$, it was shown that other MOF materials studied exhibit higher selectivity and higher retention time for $H_2S$ than $CO_2$ at 25° C. (FIG. 10). Y-1,4-NDC-fcu-MOF is the best material from the studied materials for $H_2S$ removal with retention time of 70 min/gm (5% $H_2S$, 10 $cm^3$/min flowrate). Retention time for $H_2S$ decreases for almost 40% when temperature is increased to 50° C. (FIGS. 11, 12), with highest retention time of 41 min/g (5% $H_2S$, 10 cc/min flowrate) for Y-1,4-NDC-fcu-MOF. Retention time of $H_2S$ and $CO_2$ for Y-1,4-NDC-fcu-MOF and Y-fum-fcu-MOF does not change during VSR at 25° C. (FIG. 13), while retention time for all the samples does not change during VSR at 50° C. (FIG. 14).

Figure 11:
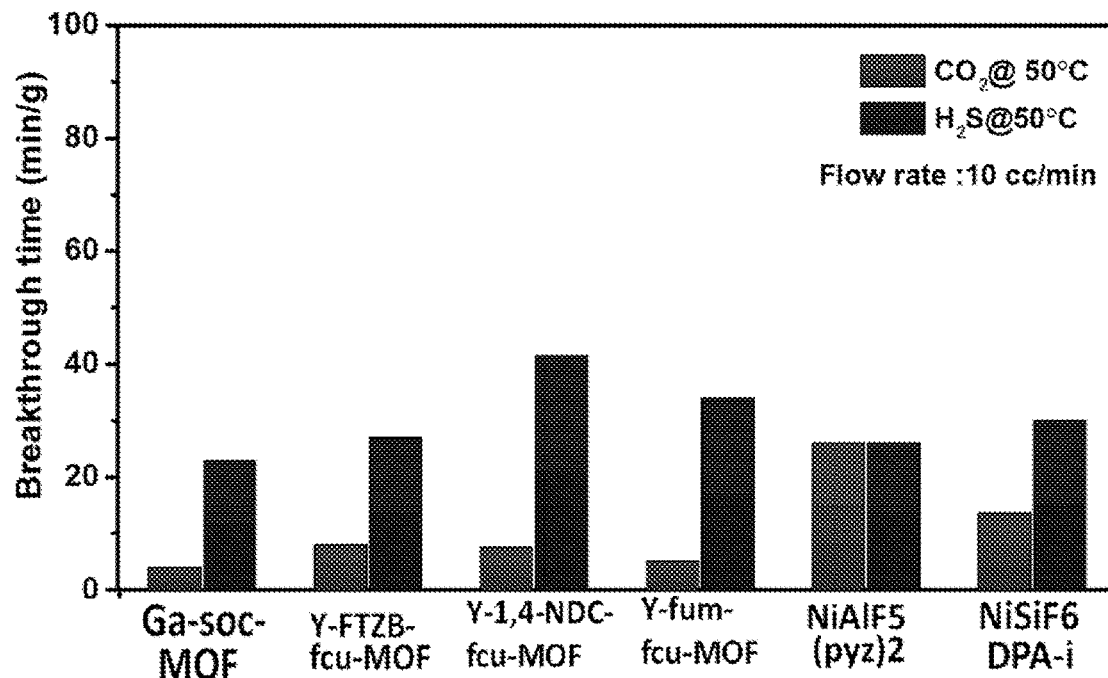
FIG. 11 illustrates a graphical view of comparison of retention time of $CO_2$ and $H_2S$ for studied materials during column breakthrough tests at 50° C. (1 bar) after optimal activation of the samples (gas mixture $CO_2/H_2S/CH_4$ (5/5/90) with 10 cm$^3$/min flow rate was used for the experiments), according to one or more embodiments of this disclosure.
Figure 12:
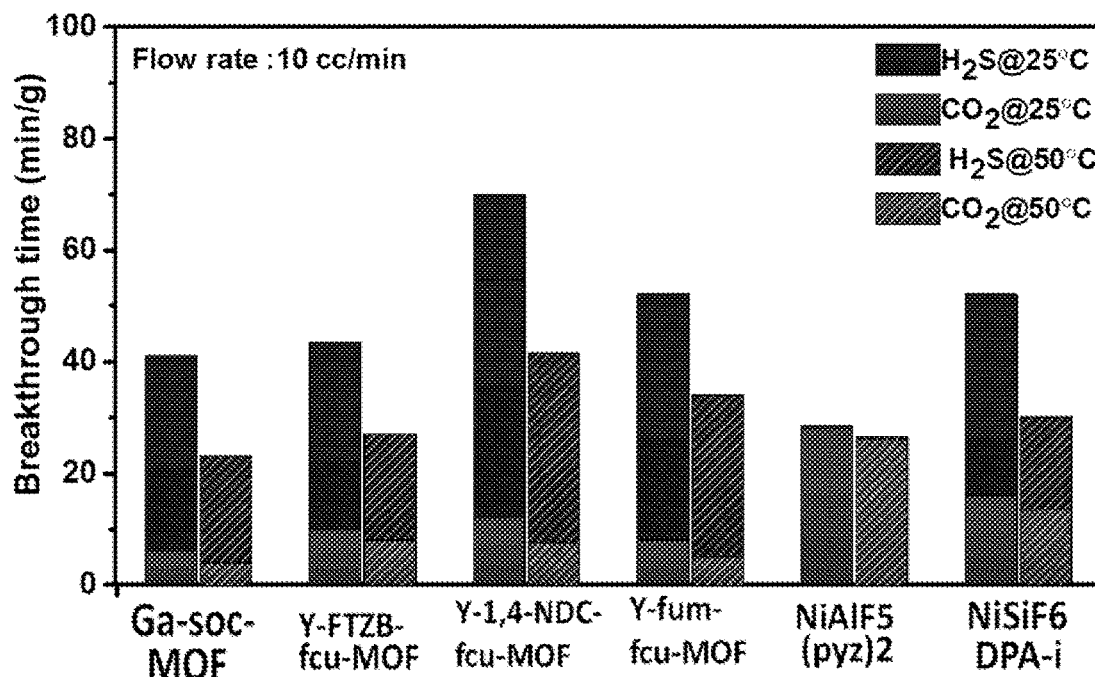
FIG. 12 illustrates a graphical view of comparison of retention time of $CO_2$ and $H_2S$ for studied materials during column breakthrough tests at 25° C. and 50° C. (1 bar) respectively after optimal activation of the samples (gas mixture $CO_2/H_2S/CH_4$ (5/5/90) with 10 cm$^3$/min flow rate was used for the experiments), according to one or more embodiments of this disclosure.

Unlike all other studied materials here, $NiAlF_5O(pyrazine)_2$ has the same retention time of 28 min/gm (5% $H_2S$, 5% $CO_2$ 10 $cm^3$/min flowrate) for both $H_2S$ and $CO_2$ at 25° C. (FIG. 10). By increasing temperature to 50° C., the retention time for $CO_2$ and $H_2S$ only decrease slightly to 26 min/gm (5% $H_2S$, 5% $CO_2$ 10 cc/min flowrate) unlike other materials (FIGS. 11, 12). During VSR at 25° C. for $NiAlF_5O$ $(pyrazine)_2$, the retention time for $H_2S$ decreases slightly (FIG. 13), however the retention time for $H_2S$ and $CO_2$ remains unchanged during VSR at 50° C. (FIG. 14). $NiAlF_5O(pyrazine)_2$ is a good candidate for simultaneous removal of $H_2S$ and $CO_2$ over the wide temperature range, while other studied materials can be good candidates for removal of $H_2S$ first and then $CO_2$ in the presence of $CH_4$ containing gas streams at 25° C.

Figure 15:
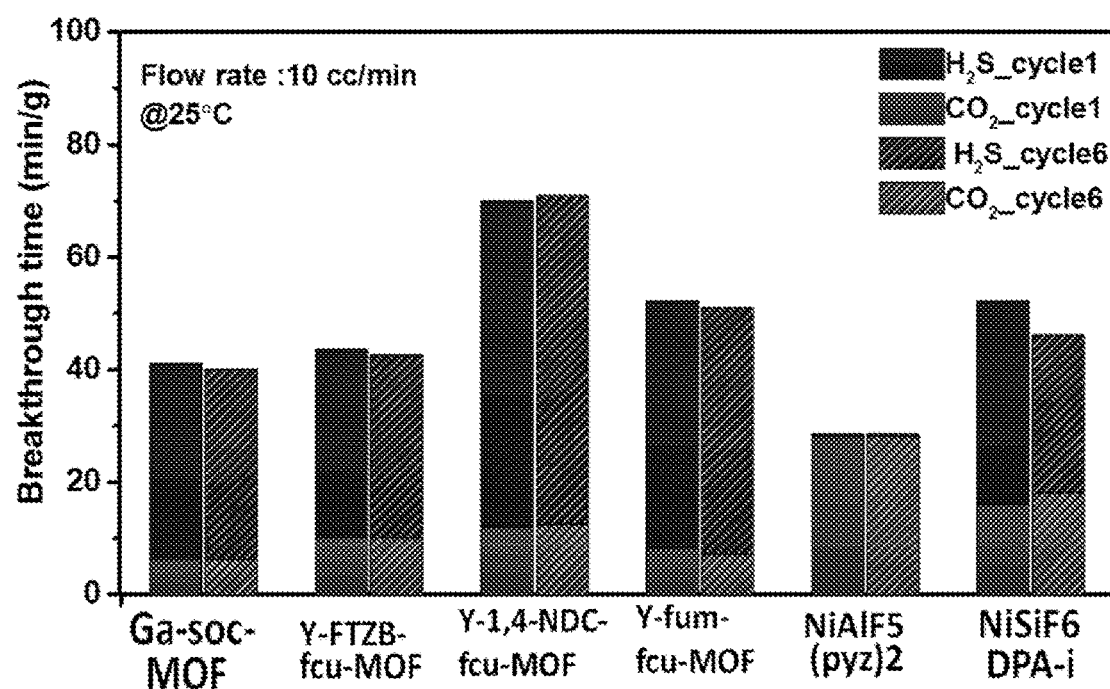
FIG. 15 illustrates a graphical view of comparison of retention time of $CO_2$ and $H_2S$ for studied materials during column breakthrough tests at 25° C. with fresh samples and samples after five breakthrough cycles respectively after optimal activation (gas mixture $CO_2/H_2S/CH_4$ (5/5/90) with 10 cm$^3$/min flow rate was used for the experiments) and comparison describes recyclability of the studied materials, according to one or more embodiments of this disclosure.

As shown in FIG. 15, uptake for all the materials remains practically unchanged between $1^{st}$ cycle and $6^{th}$ cycle under the same condition showing that all these materials selected for mixed gas testing are very stable.

The $CO_2$ and $H_2S$ uptakes for all the MOFs studied in the course of this project, using TSR and VSR mode, are reported in Tables 1 and 2.

TABLE 1

Summary of $H_2S$ and $CO_2$ adsorption uptakes of the best MOFs in TSR mode using $CO_2/H_2S/CH_4$ (5/5/90) Gas mixture (1 bar).

| Materials | $CO_2$ uptake wt % TSR mode | | $H_2S$ uptake wt % TSR mode | |
|---|---|---|---|---|
| | 298K | 323K | 298K | 323K |
| Ga-soc-MOF | 0.58 | 0.39 | 3.11 | 1.74 |
| Y-FTZB-fcu-MOF | 0.98 | 0.78 | 3.30 | 2.04 |
| Y-1,4-NDC-fcu-MOF | 1.18 | 0.74 | 5.31 | 3.14 |
| Y-fum-fcu-MOF | 0.78 | 0.49 | 3.94 | 2.58 |
| $NiAlF_5(H_2O)(pyrazine)_2(solvent)$ | 2.75 | 2.55 | 2.12 | 1.97 |
| NiSiF6 DPA-i | 1.57 | 1.32 | 3.94 | 2.27 |

* $CH_4$ uptake not detected by the flow mode system and $CO_2/CH_4$, $H_2S/CH_4$ selectivity is calculated assuming 0.1 mg as the lowest detectable uptake

TABLE 2

Summary of $H_2S$ and $CO_2$ adsorption uptakes of the best MOFs in VSR mode using $CO_2/H_2S/CH_4$ (5/5/90) at 1 bar Gas mixture (1 bar).

| Materials | $CO_2$ uptake wt % VSR mode | | $H_2S$ uptake wt % VSR mode | |
|---|---|---|---|---|
| | 298K | 323K | 298K | 323K |
| Ga-soc-MOF | 0.49 | 0.34 | 2.35 | 1.63 |
| Y-FTZB-fcu-MOF | 0.88 | 0.78 | 2.95 | 2.04 |
| Y-1,4-NDC-fcu-MOF | 1.18 | 0.78 | 5.16 | 3.19 |
| Y-fum-fcu-MOF | 0.78 | 0.59 | 3.87 | 2.58 |
| $NiAlF_5(H_2O)(pyrazine)_2(solvent)$ | 2.45 | 2.55 | 1.78 | 1.97 |
| NiSiF6 DPA-i | 1.76 | 1.32 | 3.49 | 2.28 |

Because if the low uptake of $CH_4$ vs $H_2S$ and $CO_2$ during the mixed gas tests, it was impossible to detect and quantify the $CH_4$ uptake for all the studied materials. Accordingly, in order to determine the $CO_2/CH_4$ and $CO_2/H_2S$ selectivity (Tables 3 and 4), it was assumed that the non-detectable uptake of $CH_4$ is equal the accuracy of the set-up (0.1 mg).

TABLE 3

Summary of $CO_2/CH_4$ and $H_2S/CH_4$ adsorption selectivities determined for the best MOFs in TSR mode using $CO_2/H_2S/CH_4$ (5/5/90) at 1 bar Gas mixture (1 bar).

| Materials | $CO_2/CH_4$ Selectivity* TSR mode | | $H_2S/CH_4$ Selectivity* TSR mode | |
|---|---|---|---|---|
| | 298K | 323K | 298K | 323K |
| Ga-soc-MOF | 385 | 257 | 2635 | 1478 |
| Y-FTZB-fcu-MOF | 642 | 514 | 2796 | 1735 |
| Y-1,4-NDC-fcu-MOF | 771 | 482 | 4500 | 2667 |
| Y-fum-fcu-MOF | 514 | 321 | 3342 | 2185 |
| $NiAlF_5(H_2O)(pyrazine)_2(solvent)$ | 1800 | 1671 | 1800 | 1671 |
| NiSiF6 DPA-i | 1028 | 867 | 3342 | 1928 |

*$CH_4$ uptake not detected by the flow mode system and $CO_2/CH_4$, $H_2S/CH_4$ selectivities are calculated assuming the uptake of $CH_4$ is equal to 0.1 mg, which is the lowest detectable uptake by the set-up.

TABLE 4

Summary of $CO_2/CH_4$ and $H_2S/CH_4$ adsorption selectivities determined for the best MOFs in VSR mode using $CO_2/H_2S/CH_4$ (5/5/90) at 1 bar Gas mixture (1 bar).

| Materials | $CO_2/CH_4$ Selectivity* VSR mode | | $H_2S/CH_4$ Selectivity* VSR mode | |
|---|---|---|---|---|
| | 298K | 323K | 298K | 323K |
| Ga-soc-MOF | 321 | 225 | 1992 | 1382 |
| Y-FTZB-fcu-MOF | 578 | 514 | 2507 | 1735 |
| Y-1,4-NDC-fcu-MOF | 771 | 514 | 4371 | 2700 |
| Y-fum-fcu-MOF | 514 | 385 | 3278 | 2185 |
| $NiAlF_5(H_2O)(pyrazine)_2$(solvent) | 1607 | 1671 | 1510 | 1671 |
| NiSiF6 DPA-i | 1028 | 867 | 3342 | 1928 |

*$CH_4$ uptake not detected by the flow mode system and $CO_2/CH_4$, $H_2S/CH_4$ selectivities are calculated assuming the uptake of $CH_4$ is equal to 0.1 mg, which is the lowest detectable uptake by the set-up.

Overall, all the materials selected exhibit very high selectivity for $H_2S$ vs $CH_4$. As expected, the $NiAlF_5O(pyrazine)_2$ exhibited the highest selectivity for $CO_2$. It is noted that adsorption selectivity values higher than 700-1000 are often attached with elevated degree of inaccuracy, hence, this values should be considered as infinite. Accordingly, the high values for $CO_2/CH_4$ and $H_2S/CH_4$ selectivities reported in tables 3 and 4 are highly qualitative.

In summary, highly stable recyclable MOF materials for $H_2S$ and $CO_2$ removal from natural gas with a wide range of $H_2S/CO_2$ selectivity are described that can be used for TSR and VSR at room and higher temperatures. Highly selective materials are shown for $CO_2$ having open metals sites (such as $NiAlF_5(H_2O)(pyrazine)_2$(solvent)) that have the potential to remove $CO_2$ and $H_2S$ simultaneously with high selectivity.

What is claimed is:

1. A method of capturing chemical species from a fluid composition, the method comprising
    contacting a first metal organic framework characterized by the formula $[M_aM_bF_{6-n}(O/H_2O)_w(Ligand)_x(solvent)_y]_z$ with a fluid composition including at least carbon dioxide and hydrogen sulfide, where $M_a$ is $Ni^{2+}$; $M_b$ is $Al^{3+}$, $Fe^{3+}$, $V^{3+}$ or $Nb^{5+}$; Ligand is pyrazine; n is 1; w is 1; x is 2; v is 0 to 4; solvent is a guest molecule; and z is at least equal to 1; and
    capturing carbon dioxide and hydrogen sulfide from the fluid composition.

2. The method of claim 1, wherein the fluid composition further comprises water.

3. The method of claim 1, further comprising desorbing carbon dioxide and hydrogen sulfide.

4. The method of claim 1, further comprising desorbing one or more of carbon dioxide and hydrogen sulfide.

5. The method of claim 4, wherein one or more of capturing and desorbing is effected by multicolumn pressure-temperature swing adsorption.

6. The method of claim 1, wherein carbon dioxide and hydrogen sulfide are captured from the fluid composition simultaneously.

7. The method of claim 1, wherein the metal-organic framework has open metal sites.

8. The method of claim 1, wherein the metal organic framework adsorbent is in the form of a fixed bed, a packed column, or combinations thereof.

9. The method of claim 1, wherein the fluid composition further comprises methane.

10. The method of claim 1, further comprising changing the pressure of the capture environment to alter the affinity of one or more of carbon dioxide and hydrogen sulfide for the metal organic framework adsorbent.

11. The method of claim 1, further comprising changing the temperature of the capture environment to alter the affinity of one or more of carbon dioxide and hydrogen sulfide for the metal organic framework adsorbent.

12. The method of claim 1, further comprising changing the pressure and temperature of the capture environment to alter the affinity of one or more of carbon dioxide and hydrogen sulfide for the metal organic framework adsorbent.

13. The method of claim 1, wherein capturing comprises physical adsorption of the one or more captured chemical species by the metal organic framework.

14. The method of claim 1, wherein capturing comprises chemisorption of the one or more captured chemical species by the metal organic framework.

15. The method of claim 14, wherein chemisorption occurs by one or more captured chemical species chemically interacting with one or more open metal sites of the metal organic framework.

16. The method of claim 1, simultaneously or separately contacting the fluid composition with a second metal organic framework, characterized by the formula $[M_cM_dF_{6-n}(O/H_2O)_w(Ligand)_x(solvent)_y]_z$, wherein n is 1; w is 1; x is 2; y is 0 to 4; and solvent is a guest molecule; wherein $M_c$ comprises $Ni^{+2}$ and $M_d$ comprises $Al^{+3}$, $Fe^{+2}$, or $Fe^{+3}$, wherein the second metal organic framework is different from the first metal organic framework.

17. The method of claim 16, wherein the first metal organic framework is characterized by the formula $[NiNbF_{6-n}(O/H_2O)_w(Ligand)_x(solvent)_y]_z$; wherein n is 1; w is 1; x is 2; y is 0 to 4; and solvent is a guest molecule.

* * * * *

UNITED STATES PATENT AND TRADEMARK OFFICE
CERTIFICATE OF CORRECTION

PATENT NO. : 10,328,380 B2
APPLICATION NO. : 15/564935
DATED : June 25, 2019
INVENTOR(S) : Mohamed Eddaoudi et al.

Page 1 of 1

It is certified that error appears in the above-identified patent and that said Letters Patent is hereby corrected as shown below:

In the Claims

Column 13 Claim 1, Line 43 reads:
"v is 0 to 4"
But it should read:
"y is 0 to 4".

Signed and Sealed this
Second Day of June, 2020

Andrei Iancu
*Director of the United States Patent and Trademark Office*